US008513297B2

(12) United States Patent
Boiteau et al.

(10) Patent No.: US 8,513,297 B2
(45) Date of Patent: Aug. 20, 2013

(54) BIAROMATIC COMPOUNDS THAT MODULATE PPARγ TYPE RECEPTORS AND COSMETIC/PHARMACEUTICAL COMPOSITIONS COMPRISED THEREOF

(75) Inventors: Jean-Guy Boiteau, Saint-Aunes (FR); Laurence Clary, Le Colle sur Loup (FR); Corinne Millois Barbuis, Saint-Raphael (FR)

(73) Assignee: Galderma Research & Development, Biot (FR)

( * ) Notice: Subject to any disclaimer, the term of this patent is extended or adjusted under 35 U.S.C. 154(b) by 0 days.

(21) Appl. No.: 13/353,125

(22) Filed: Jan. 18, 2012

(65) Prior Publication Data

US 2012/0121527 A1 May 17, 2012

Related U.S. Application Data

(60) Division of application No. 11/802,234, filed on May 21, 2007, now Pat. No. 8,129,416, which is a continuation of application No. PCT/EP2005/013533, filed on Nov. 17, 2005.

(60) Provisional application No. 60/631,989, filed on Dec. 1, 2004.

(30) Foreign Application Priority Data

Nov. 19, 2004 (FR) ..................... 04 12326

(51) Int. Cl.
*C07D 333/24* (2006.01)
*A61K 31/381* (2006.01)

(52) U.S. Cl.
USPC ............... 514/438; 514/444; 549/59; 549/77

(58) Field of Classification Search
USPC ............... 549/59, 77; 514/438, 444
See application file for complete search history.

(56) References Cited

U.S. PATENT DOCUMENTS

| 6,927,228 | B2 | 8/2005 | Bernardon et al. |
| 7,285,568 | B2 | 10/2007 | Clary et al. |
| 7,294,639 | B2 | 11/2007 | Bernardon et al. |
| 7,307,078 | B2 | 12/2007 | Clary et al. |
| 2005/0256116 | A1 | 11/2005 | Clary et al. |

FOREIGN PATENT DOCUMENTS

| FR | 2833949 A1 | 6/2003 |
| FR | 2847251 A1 | 5/2004 |
| FR | 2847580 A1 | 5/2004 |
| FR | 2848553 A1 | 6/2004 |
| WO | WO 02/12210 A1 | 2/2002 |
| WO | WO 2004/024939 A2 | 3/2004 |
| WO | WO 2004/113331 A1 | 12/2004 |

OTHER PUBLICATIONS

International Search Report issued on May 12, 2006 by the European Patent Office in corresponding International Patent Application No. PCT/EP2005/013533.
Written Opinion of the International Searching Authority issued on May 11, 2006 by the European Patent Office in corresponding International Patent Application No. PCT/EP2005/013533.
Fayer et al., "Lack of correlation between in vitro inhibition of CYP3A-mediated metabolism by a PPAR-gamma agonist and its effect on the clinical pharmacokinetics of midazolam, an in vivo probe of CYP3A activity," PubMed Abstract *J. Clin. Pharmacol.*, Mar. 2001, pp. 305-316, vol. 41, No. 3, American College of Clinical Pharmacology, US.
Simone, "Oncology: Introduction," *Cecil Textbook of Medicine*, 1996, pp. 1004-1010, Edition 20, vol. 1, W. B. Saunders Company, US.

*Primary Examiner* — Deepak Rao
(74) *Attorney, Agent, or Firm* — Dentons US LLP

(57) ABSTRACT

Novel biaromatic compounds having the general formula (I):

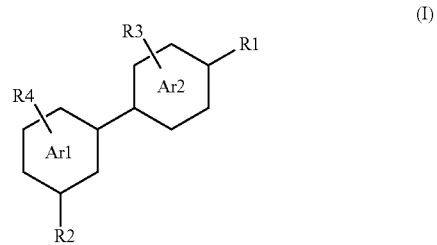

and cosmetic/pharmaceutical compositions comprised thereof are useful in human or veterinary medicine (in dermatology and also in the fields of cardiovascular diseases, of immune diseases and/of diseases related to the metabolism of lipids), or, alternatively, in cosmetic compositions.

27 Claims, 4 Drawing Sheets

BIAROMATIC COMPOUNDS THAT MODULATE PPARγ TYPE RECEPTORS AND COSMETIC/PHARMACEUTICAL COMPOSITIONS COMPRISED THEREOF

CROSS REFERENCE TO EARLIER APPLICATIONS

This application is a division of copending U.S. application Ser. No. 11/802,234, filed May 21, 2007, now allowed, which is a continuation of PCT/EP 2005/013533 filed Nov. 17, 2005 and designating the United States, published in the English language as WO 2006/053791 A3 on May 26, 2006, which claims benefit of U.S. Provisional Application No. 60/631,989, filed Dec. 1, 2004 and also claims priority of FR04/12326, filed Nov. 19, 2004, each hereby expressly incorporated by reference in its entirety and each assigned to the assignee hereof.

BACKGROUND OF THE INVENTION

1. Technical Field of the Invention

The present invention relates to, as novel and useful industrial products, a novel class of compounds that are modulators of receptors of Peroxisome Proliferator-Activated Receptor type of subtype γ (PPARγ). This invention also relates to a process for the preparation of same and to their formulation into pharmaceutical compositions useful in human or veterinary medicine, or, alternatively, into cosmetic compositions.

2. Description of Background and/or Related and/or Prior Art

The activity of receptors of PPAR type has been the subject of many studies. See, for example, the publication entitled "Differential Expression of Peroxisome Proliferator-Activated Receptor Subtypes During the Differentiation of Human Keratinocytes", Michel Rivier et al., *J. Invest. Dermatol.*, 111, 1998, pp. 1116-1121, in which is listed a large number of bibliographic references relating to receptors of PPAR type. See also the report entitled "The PPARs: From orphan receptors to Drug Discovery", Timothy M. Willson, Peter J. Brown, Daniel D. Sternbach and Brad R. Henke, *J. Med. Chem.*, 2000, Vol. 43, pp. 527-550.

PPAR receptors activate transcription by binding to elements of DNA sequences, known as peroxisome proliferator response elements (PPRE), in the form of a heterodimer with retinoid X receptors (known as RXRs).

Three subtypes of human PPARs have been identified and described: PPARα, PPARγ and PPARδ (or NUC1).

PPARα is mainly expressed in the liver, while PPARδ is ubiquitous.

PPARγ is the most extensively studied of the three subtypes. All the references suggest a critical role of PPARγ in regulating the differentiation of adipocytes, where it is greatly expressed. It also plays a key role in systemic lipid homeostasis.

It has been described, in particular, in WO 96/33724 that PPARγ-selective compounds, such as a prostaglandin-J2 or -D2, are potential active agents for treating obesity and diabetes.

Moreover, the assignee hereof has already described PPARγ compounds and/or the use thereof in FR-2,773,075, which describes the use of PPARγ activator compounds in the preparation of a pharmaceutical composition, the composition being useful to treat skin disorders associated with an anomaly of epidermal cell differentiation.

SUMMARY OF THE INVENTION

The present invention features a novel class of PPARγ-modulating compounds that show very good specific affinity for PPARγ.

Thus, the present invention features novel biaromatic compounds having the general formula (I) below:

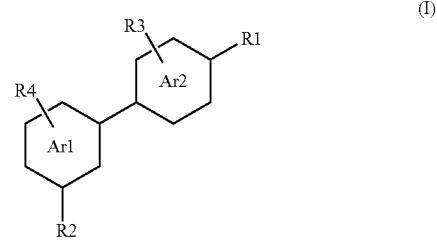

in which:

R1 is a radical of formula (a) or (b) below:

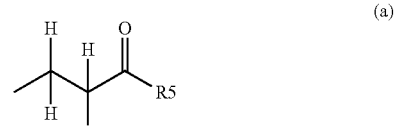

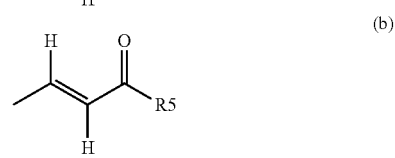

wherein R5 is as defined below;

R2 is a radical of formula $(CH_2)_m-NR_6-CQ-(NH)_nR_7$, wherein Q, R6, R7, m and n are as defined below;

R3 and R4, which may be identical or different, are each a hydrogen atom, a halogen atom, a linear or cyclic alkyl radical having from 1 to 12 carbon atoms that may be interrupted with oxygen, fluorine or nitrogen atoms, a hydroxyl radical, an alkoxy radical having from 1 to 10 carbon atoms, a polyether radical, an aralkyl radical or an aryloxy radical;

R5 is a hydroxyl radical, a radical OR8 or a hydroxylamine radical, wherein R8 is as defined below;

R6 is a lower alkyl radical having from 1 to 4 carbon atoms;

R7 is an alkyl radical having from 1 to 12 carbon atoms, an aryl radical, an aralkyl radical, a heteroaryl radical or a heterocyclic radical;

R8 is an alkyl, aryl or aralkyl radical;

m and n have the values 0 or 1;

Q is an oxygen or sulfur atom;

Ar1 and Ar2, which may be identical or different, are each an optionally substituted aromatic radical of one of the formulae:

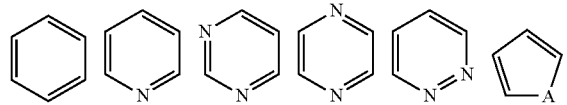

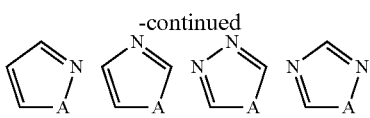

A is a sulfur or oxygen atom or a radical N—R9;

R9 is a hydrogen atom or an alkyl radical having from 1 to 12 carbon atoms;

with the proviso that when Ar1 or Ar2 is an aryl radical, then Ar2 or Ar1 is necessarily a heteroaryl radical, and the optical and geometrical isomers of said compounds of formula (I), and also the salts thereof.

In particular, when the compounds according to the invention are in the form of salts, they are salts of an alkali metal, in particular a sodium or potassium salt, or salts of an alkaline-earth metal or salts of organic amines, more particularly of amino acids such as arginine or lysine. In the case of compounds containing nitrogen heterocycles, the salts may be of mineral or organic acids.

Figure 1:
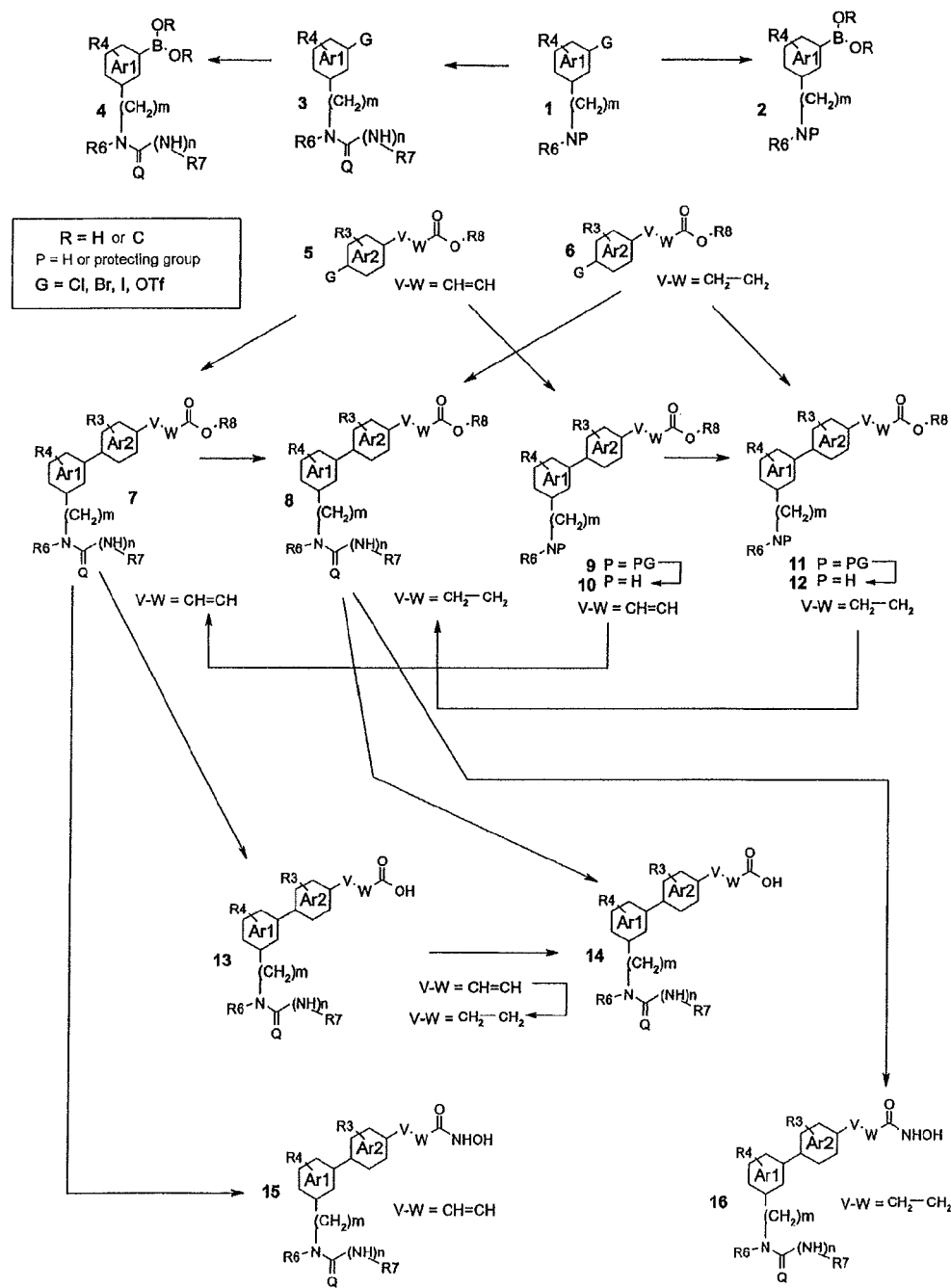
FIGS. 1-4 show a variety of reaction schemes for the ultimate preparation of the biaromatic compounds according to the present invention.

DETAILED DESCRIPTION OF BEST MODE
AND SPECIFIC/PREFERRED EMBODIMENTS
OF THE INVENTION

According to the present invention, the term "hydroxyl radical" means an —OH radical.

The term "halogen atom" means a fluorine, chlorine or bromine atom.

According to the present invention, the term "alkyl radical having from 1 to 12 carbon atoms" means a saturated or unsaturated, linear or cyclic, optionally branched, hydrogenated or fluorinated radical having from 1 to 12 carbon atoms, which may be interrupted with a hetero atom, and the alkyl radicals having from 1 to 12 carbon atoms are preferably methyl, ethyl, isopropyl, butyl, isobutyl, tert-butyl, hexyl, heptyl, octyl, decyl, cyclopentyl, cyclohexyl or methylenecyclopropyl radicals.

The alkyl radicals having from 1 to 4 carbon atoms will preferably be methyl, ethyl, n-propyl, i-propyl, c-propyl, methylcyclopropyl, n-butyl, i-butyl or t-butyl radicals.

The term "alkoxy radical having from 1 to 7 carbon atoms" means a methoxy, ethoxy, isopropyloxy, methylcyclopropyloxy, isobutoxy, tert-butoxy, pentyloxy, isopentyloxy, hexyloxy, heptyloxy, benzyloxy, aryloxy or phenoxy radical, which may be optionally substituted with an alkyl radical having from 1 to 12 carbon atoms or an alkoxy radical having from 1 to 5 carbon atoms.

The term "polyether radical" means a polyether radical having from 1 to 6 carbon atoms interrupted with at least one oxygen atom, such as methoxymethoxy, ethoxymethoxy or methoxyethoxymethoxy radicals.

The term "aralkyl radical" means a benzyl, phenethyl or 2-naphthylmethyl radical, which may be mono- or disubstituted with a halogen atom, a $CF_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl having from 1 to 12 carbon atoms.

The term "aryl radical" means a phenyl, biphenyl, cinnamyl or naphthyl radical, which may be mono- or disubstituted with a halogen atom, a $CF_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl having from 1 to 12 carbon atoms.

The term "heteroaryl radical" means an aryl radical interrupted with one or more hetero atoms, such as a pyridyl, furyl, thienyl, isoxazolyl, oxadiazolyl, oxazolyl, isothiazolyl, quinazolinyl, benzothiadiazolyl, benzimidazolyl, quinoxalyl, indolyl or benzofuryl radical, optionally substituted with at least one halogen, an alkyl radical having from 1 to 12 carbon atoms, an alkoxy radical having from 1 to 7 carbon atoms, an aryl radical, a nitro function, a polyether radical, a heteroaryl radical, a benzoyl radical, an alkyl ester group, a carboxylic acid, a hydroxyl group optionally protected with an acetyl or benzoyl group or an amino function optionally protected with an acetyl or benzoyl group or optionally substituted with at least one alkyl radical having from 1 to 12 carbon atoms.

The term "heterocyclic radical" preferably means a morpholino, piperidino, piperazino, 2-oxo-1-piperidyl or 2-oxo-1-pyrrolidinyl radical, optionally substituted with at least one alkyl radical having from 1 to 12 carbon atoms, an alkoxy radical having from 1 to 7 carbon atoms, an aryl radical, a nitro function, a polyether radical, a heteroaryl radical, a benzoyl radical, an alkyl ester group, a carboxylic acid, a hydroxyl group optionally protected with an acetyl or benzoyl group or an amino function optionally protected with an acetyl or benzoyl group or optionally substituted with at least one alkyl having from 1 to 12 carbon atoms.

Exemplary compounds of formula (I) according to the present invention, whether alone or as a mixture, include:
1. 3-(5-{3-[(Methyloctanoylamino)methyl]phenyl}thiophen-2-yl)acrylic acid,
2. 3-(5-{3-[(Methyloctanoylamino)methyl]phenyl}thiophen-2-yl)propanoic acid,
3. 3-(5-{3-[(Methyloctanoylamino)methyl]phenyl}furan-2-yl)acrylic acid,
4. 3-(4-{5-[(Methyloctanoylamino)methyl]thiophen-3-yl}phenyl)acrylic acid,
5. 3-(4-{5-[(Methyloctanoylamino)methyl]thiophen-3-yl}phenyl)propanoic acid,
6. 3-{4-[6-(3-Heptyl-1-methylureido)pyrid-2-yl]phenyl}propanoic acid,
7. 3-{6-[3-(3-Heptyl-1-methylureido)phenyl]pyrid-3-yl}propanoic acid,
8. 2-[4-(2-Carboxyethyl)phenyl]-4-(3-heptyl-1-methylureido)pyridinium acetate,
9. 3-{5-[3-(3-Pentyl-1-methylureido)phenyl]pyrimidin-2-yl}acrylic acid,
10. 3-{5-[3-(3-Pentyl-1-methylureido)phenyl]pyrimidin-2-yl}propanoic acid,
11. 2-[2-Butoxy-4-(2-carboxyethyl)phenyl]-6-(1-methyl-3-pentylureido)pyridinium hydrochloride,
12. 2-[2-Butoxy-4-(2-carboxyethyl)phenyl]-6-(1-methyl-3-butylureido)pyridinium hydrochloride,
13. 2-[4-(2-Carboxyethyl)-2-ethoxyphenyl]-6-(3-heptyl-1-methylureido)pyridinium hydrochloride, 14. 3-(3-Butoxy-4-{5-[(methyloctanoylamino)methyl]thiophen-3-yl}phenyl)propanoic acid,
15. 3-(3-Butoxy-4-(5-{[(4-methoxybenzoyl)methylamino]methyl}thiophen-3-yl)phenyl]propanoic acid,
16. 3-(3-Butoxy-4-(5-{[(3-methoxybenzoyl)methylamino]methyl}thiophen-3-yl)phenyl]propanoic acid,
17. 3-{5-[4-(3-Heptyl-1-methylureido)pyrid-2-yl]furan-2-yl}propanoic acid,
18. 3-[5-[3-(3-Heptyl-1-methylureido)phenyl]-4-(2,2,2-trifluoroethoxy)furan-2-yl]propanoic acid,
19. 3-(5-{3-[3-(3,5-Dimethoxyphenyl)-1-ethylureido]phenyl}-3-methylfuran-2-yl)propanoic acid,
20. 3-(5-{6-[3-(4-Ethoxyphenyl)-1-ethylureido]pyrid-2-yl}furan-2-yl)propanoic acid,
21. 3-(2-Methyl-4-{6-[1-methyl-3-(4-methylpentyl)ureido]pyrid-2-yl}phenyl)propanoic acid,
22. Methyl 3-{-4-[6-(1-ethyl-3-naphthalen-2-ylureido)pyrid-2-yl]-2-fluorophenyl}propanoate,
23. 3-(4-{6-[3-(4-Butoxyphenyl)-1-methylureido]pyrid-2-yl}phenyl)-N-hydroxypropionamide,
24. 3-{3-Cyclopropylmethoxy-4-[6-(1-methyl-3-pentylureido)pyrid-2-yl]phenyl}propanoic acid,
25. 3-{-4-[6-(1-Ethyl-3-phenylthioureido)pyrid-2-yl]-3-propoxyphenyl}propanoic acid,
26. 3-{3-Ethoxy-4-[6-(3-heptyl-1-methylureido)pyrid-2-yl]phenyl}propanoic acid,
27. 3-{4-[6-(3-Hexyl-1-methylureido)pyrid-2-yl]-3-isopropoxyphenyl}propanoic acid,
28. 3-[4-[6-(3-Heptyl-1-methylureido)pyrid-2-yl]-3-(4,4,4-trifluorobutoxy)phenyl]propanoic acid,
29. 3-{3-(2-Dimethylaminoethoxy)-4-[6-(1-methyl-3-pentylureido)pyrid-2-yl]phenyl}propanoic acid,
30. 3-{3-(3-Hydroxypropoxy)-4-[6-(1-methyl-3-pentylureido)pyrid-2-yl]phenyl}propanoic acid,
31. 3-{4-[6-(1-Ethyl-3-phenylthioureido)pyrid-2-yl]-3-fluorophenyl}acrylic acid,
32. 3-{4-[6-(3-Hexyl-1-methylureido)pyrid-2-yl]-3-trifluoromethylphenyl}propanoic acid,
33. 3-[6'-(1-Methyl-3-phenethylureido)[2,2']bipyridinyl-5-yl]propanoic acid,
34. 3-{2-[6-(3-Hexyl-1-methylureido)pyrid-2-yl]thiazol-4-yl}propanoic acid,
35. Ethyl 3-{2-[6-(3-hexyl-1-methylureido)pyrid-2-yl]thiazol-5-yl}propanoate,
36. 3-(3-{6-[1-Methyl-3-(6-methylheptyl)ureido]pyrid-2-yl}isoxazol-5-yl)propanoic acid,
37. 3-{4-[2-(3-Heptyl-1-methylureido)pyrimidin-4-yl]phenyl}propanoic acid,
38. 3-{3-Cyclopropylmethoxy-4-[2-(3-heptyl-1-methylureido)pyrimidin-4-yl]phenyl}propanoic acid,
39. 3-(4-{2-[1-Ethyl-3-(4-propoxyphenyl)ureido]pyrimidin-4-yl}-3-fluorophenyl)propanoic acid,
40. 3-{2-Fluoro-4-[2-(1-methyl-3-naphthalen-2-ylureido)pyrid-4-yl]phenyl}-N-hydroxypropionamide,
41. 3-[2'-(3-Hexyl-1-methylthioureido)[2,4]bipyridinyl-5-yl]propanoic acid,
42. 3-{4-[2-(3-Hexyl-1-methylureido)pyrid-4-yl]-3-propoxyphenyl}propanoic acid,
43. 3-(3-Benzyloxy-4-{4-[1-methyl-3-(5-methylhexyl)ureido]pyrid-2-yl}phenyl)propanoic acid,
44. 3-{2-[4-(3-Hexyl-1-methylureido)pyrid-2-yl]thiazol-5-yl}acrylic acid,
45. 3-{5-[3-(3-Hexyl-1-methylureido)phenyl]pyrid-2-yl}acrylic acid,
46. 3-{5-[5-(3-Heptyl-1-methylthioureido)thiophen-3-yl]pyrid-2-yl}acrylic acid,
47. 3-{4-[2-(3-Heptyl-1-methylureido)thiazol-4-yl]-3-propoxyphenyl}propanoic acid,
48. 3-(2-Fluoro-4-{5-[(heptanoylmethylamino)methyl]thiophen-3-yl}phenyl)propanoic acid,
49. 3-(4-{5-[(Heptanoylmethylamino)methyl]thiophen-3-yl}-3-isobutoxyphenyl)acrylic acid,
50. 3-(3-(2-Cyclopentylethoxy)-4-{5-[(methyloctanoylamino)methyl]thiophen-3-yl}phenyl)propanoic acid,
51. Methyl 3-(3-isobutoxy-4-{5-[(methylnonanoylamino)methyl]thiophen-3-yl}phenyl)propanoate,
52. 3-{6-[5-({Ethyl-[2-(2-pentylphenyl)acetyl]amino}methyl)thiophen-3-yl]pyrid-3-yl}propanoic acid,
53. 3-(4-{4-[(Methylnonanoylamino)methyl]thiazol-2-yl}-3-propoxyphenyl)propanoic acid,
54. 3-(2-Chloro-4-{4-[(methylnonanoylamino)methyl]thiophen-2-yl}phenyl)propanoic acid,
55. 3-(2-Fluoro-4-{4-[(methylnonanoylamino)methyl]thiophen-2-yl}phenyl)acrylic acid,
56. 3-(4-{4-[(Heptanoylmethylamino)methyl]thiophen-2-yl}-1-methyl-1H-pyrrol-2-yl)propanoic acid,
57. 3-(4-{4-[(Heptanoylmethylamino)methyl]thiophen-2-yl}furan-2-yl)propanoic acid,
58. 3-{5'-[(Heptanoylmethylamino)methyl][3,3']bithiophenyl-5-yl}propanoic acid,
59. Phenyl 3-{5'-[(heptanoylmethylamino)methyl]-3-propyl[2,3']bithiophenyl-5-yl}propanoate,
60. 3-(5-{5-[(Heptanoylmethylamino)methyl]thiophen-3-yl}-4-propylfuran-2-yl)acrylic acid,
61. 3-{3-Butoxy-4-[6-(3-heptyl-1-methylureido)pyrid-2-yl]phenyl}propanoic acid,
62. 3-{3-Benzyloxy-4-[6-(3-heptyl-1-methylureido)pyrid-2-yl]phenyl}propanoic acid,
63. 3-{3-Benzyloxy-4-[2-(3-heptyl-1-methylureido)pyrimidin-4-yl]phenyl}propanoic acid,
64. 3-{3-Butyloxy-4-[2-(3-heptyl-1-methylureido)pyrimidin-4-yl]phenyl}propanoic acid,
65. 3-{3-Butoxy-4-[4-(3-heptyl-1-methylureido)pyrid-2-yl]phenyl}propanoic acid,
66. 3-{3-Benzyloxy-4-[4-(3-heptyl-1-methylureido)pyrid-2-yl]phenyl}propanoic acid,
67. 3-{3-Benzyloxy-4-[5-(3-heptyl-1-methylureido)pyrid-3-yl]phenyl}propanoic acid,
68. 3-{3-Butoxy-4-[5-(3-heptyl-1-methylureido)pyrid-3-yl]phenyl}propanoic acid,
69. 3-(5-{3-[(Methyloctanoylamino)methyl]phenyl}-4-propylthiophen-2-yl)propanoic acid,
70. 3-(3-Benzyloxy-4-{5-[(methyloctanoylamino)methyl]thiophen-3-yl{phenyl)propanoic acid,
71. 3-(4-Benzyl-5-{3-[(hexanoylmethylamino)methyl]phenyl}thiophen-2-yl)propanoic acid,
72. 3-{4-Cyclopropylmethyl-5-[3-(1-methyl-3-pentylureido)phenyl]thiophen-2-yl}propanoic acid,
73. 3-{5-[3-(1-Methyl-3-pentylureido)-4-trifluoromethylphenyl]thiophen-2-yl}propanoic acid,
74. 3-(5-{3-[3-(4-Butoxyphenyl)-1-ethylureido]phenyl}thiophen-2-yl)propanoic acid,
75. 3-{5-[3-(3-Heptyl-1-methylureido)-4-trifluoromethylphenyl]furan-2-yl}propanoic acid,
76. 3-{2-Butoxy-4-[6-(1-methyl-3-pentylureido)pyrid-2-yl]phenyl}propanoic acid,
77. 3-{2-(4-Methoxybenzyloxy)-4-[6-(1-methyl-3-pentylureido)pyrid-2-yl]phenyl}propanoic acid,
78. 3-{2-(3-Methoxybenzyloxy)-4-[6-(1-methyl-3-pentylureido)pyrid-2-yl]phenyl}propanoic acid, 79. 3-[2-Cyclopropylmethoxy-4-(6-{3-[2-(4-methoxyphenyl)ethyl]-1-methylureido}pyrid-2-yl)phenyl]propanoic acid According to the present invention, the compounds of formula (I) that are more particularly preferred are those which satisfy at least one of the following characteristics:

R3 is an alkoxy radical having from 1 to 7 carbon atoms;
R5 is to a hydroxyl radical;
the sequence —$(CH_2)_m$—$NR_6$—$CQ(NH)_n R_7$ wherein m=0, n=1;
Q is an oxygen atom;
R7 is an alkyl radical having from 1 to 8 carbon atoms;
at least Ar1 or Ar2 is a group of pyridine type.

The present invention also features processes for preparing the compounds of formula (I), in particular according to the reaction schemes shown in FIGS. 1, 2, 3 and 4.

FIG. 1: The boronic acid or ester 2 may be obtained from compound 1 under standard conditions, for example by reaction with tert-butyllithium followed by an addition to the trimethyl borate or reaction with pinacoldiborane in the presence of a palladium catalyst, for instance diphenylphosphinoferrocenepalladium dichloride. Compound 1 may also be directly coupled with an isocyanate, a thioisocyanate or an acyl chloride (in this case n=0) under standard conditions to give compound 3.

The boronic acid or ester 4 may be obtained from compound 3 under standard conditions, for example by reaction with tert-butyllithium followed by an addition to trimethyl borate or reaction with pinacoldiborane in the presence of a palladium catalyst, for instance diphenylphosphinoferrocenepalladium dichloride.

The compounds 5 may either be purchased commercially or may be synthesized from the corresponding aldehyde thereof via a Wittig reaction.

A Suzuki type palladium coupling from the boronate 4 or 2 and compound 5 (selected from an aryl bromide, iodide, chloride or triflate) allows the compounds having the aryl-aryl sequence 7 or 9, respectively, to be obtained.

A Suzuki type palladium coupling from the boronate 4 or 2 and compound 6 (selected from an aryl bromide, iodide, chloride or triflate) allows the compounds having the aryl-aryl sequence 8 or 11, respectively, to be obtained.

Compounds 10 and 12 may be obtained from compounds 9 and 11 by deprotection under standard conditions, for example by treatment with a strong acid, for instance trifluoroacetic acid if P is a Boc group.

Compounds 10 and 12 may be coupled with isocyanates, thioisocyanates or acyl chlorides (in this case n=0) under the standard conditions to give the compounds 7 and 8 respectively.

Compounds 8 and 11 may be obtained via hydrogenation of compounds 7 and 9 under standard hydrogenation conditions, for instance: hydrogen catalyzed with palladium-on-charcoal.

The acid functions of compounds 13 and 14 may be obtained from compounds 7 and 8 respectively: via saponification if R8 is an alkyl chain, using a base, for instance sodium hydroxide.

Compound 14 may be obtained via hydrogenation of compound 13 under standard hydrogenation conditions, for instance: hydrogen catalyzed with palladium-on-charcoal.

Compounds 15 and 16 may be obtained from the esters 7 and 8, respectively, via treatment with hydroxylamine.

Figure 2:
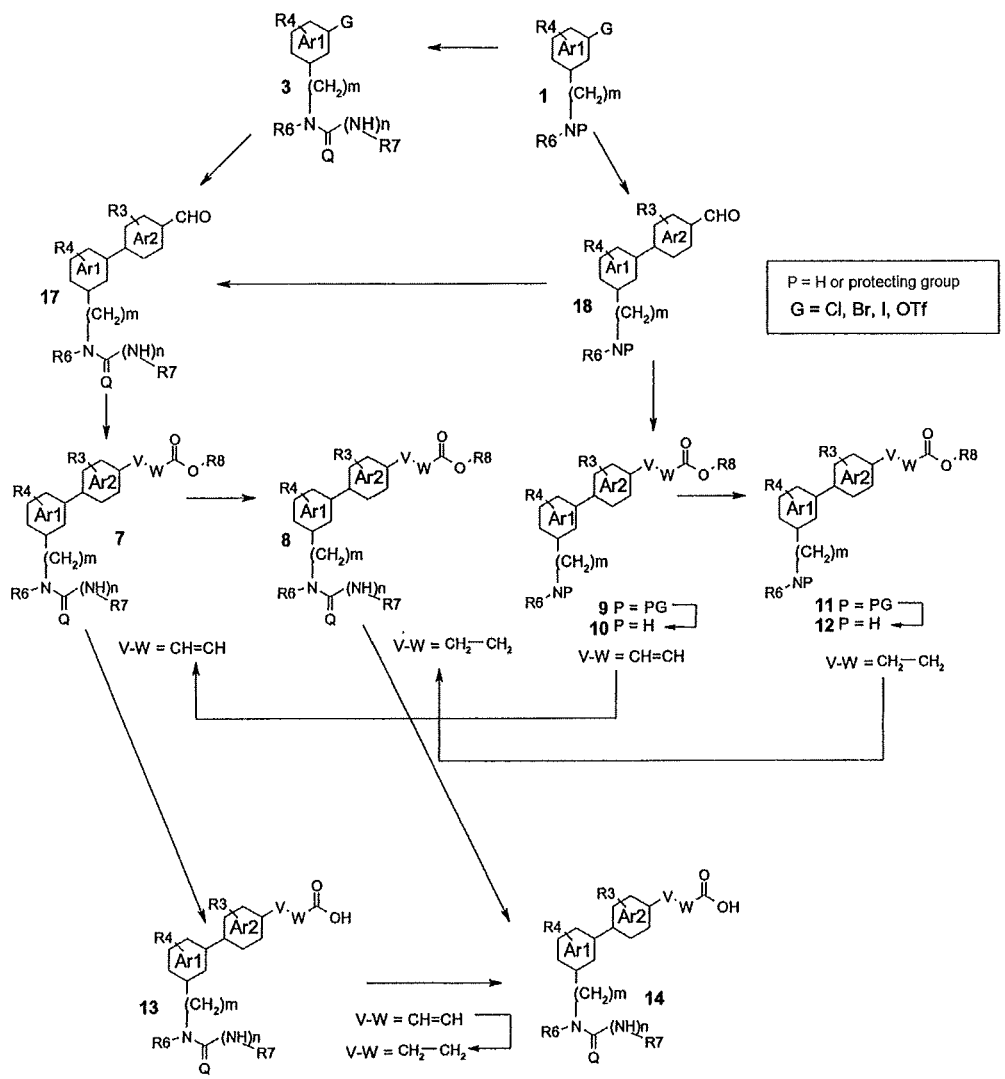

FIG. 2: A Suzuki type palladium coupling between a commercial arylboronic acid containing a formyl group and compounds 1 or 3 (selected from an aryl bromide, iodide, chloride or triflate) allows the compounds having the aryl-aryl sequence 18 or 17, respectively, to be obtained.

Compound 18 may be coupled with isocyanates, thioisocyanates or acyl chlorides (in this case n=1) under standard conditions to give compound 17.

Compounds 7 and 9 may be obtained via a Wittig reaction starting with compounds 17 and 18, respectively, for example via the action of methyl triphenylphosphoranylideneacetate.

Figure 3:
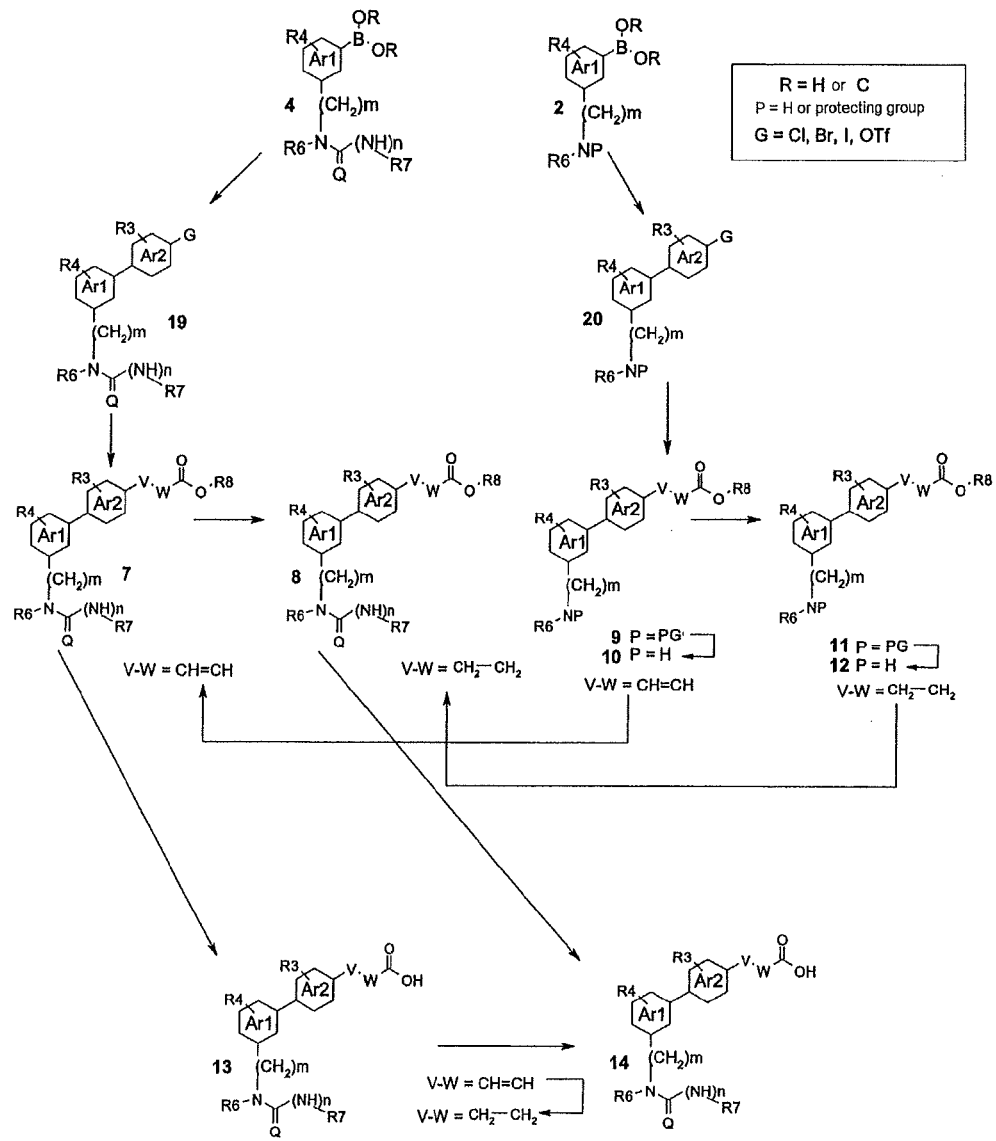

FIG. 3: A Suzuki type palladium coupling between the boronic acids or esters 4 or 2 and aryl dihalides selected from bromides, iodides and chlorides allows the compounds having the aryl-aryl sequence 19 or 20, respectively, to be obtained.

Compounds 7 and 9 may be obtained from compounds 19 and 20, respectively, via a Heck type palladium coupling with alkyl or aryl acrylates.

Figure 4:
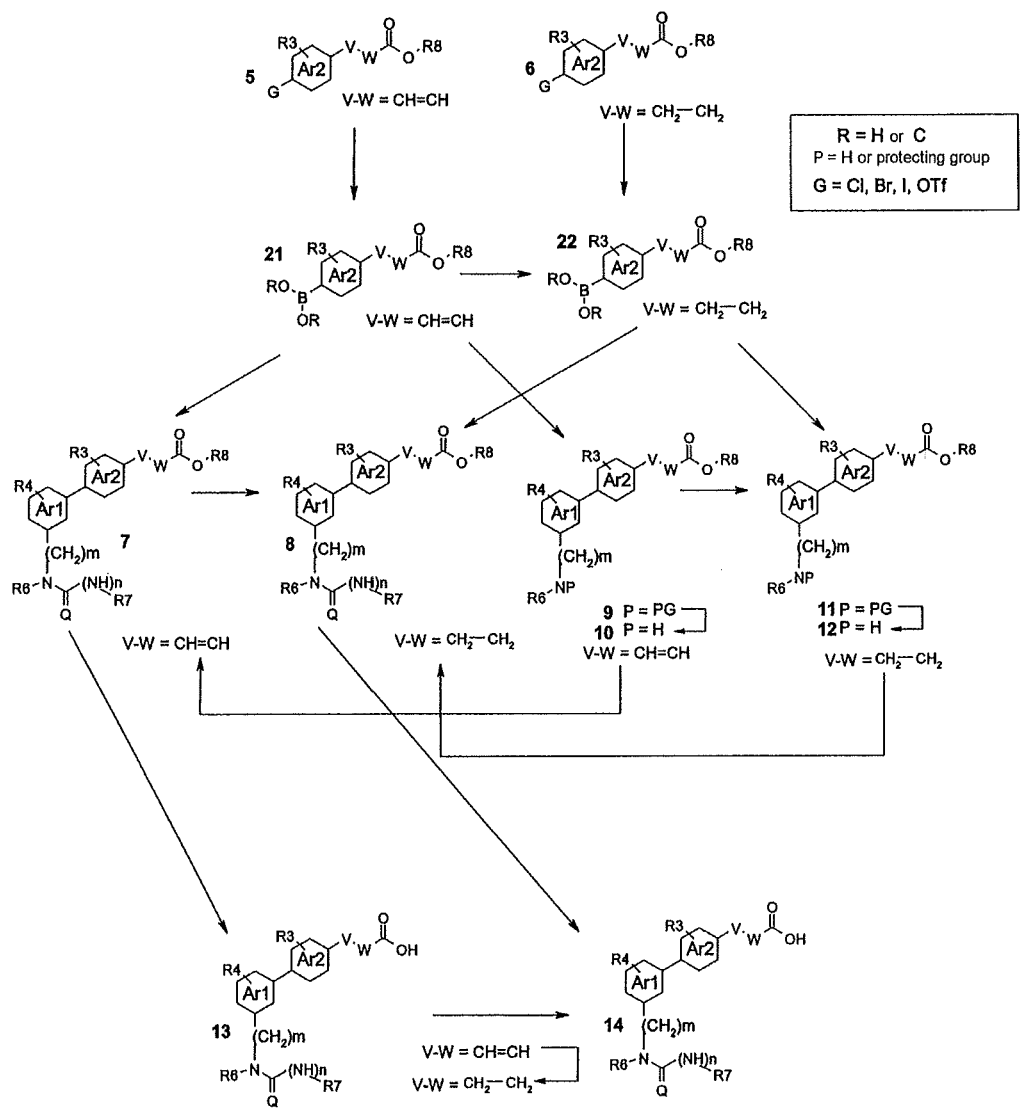

FIG. 4: The boronates 21 and 22 may be obtained by treating compounds 5 and 6, respectively, with pinacoldiborane, in the presence of a palladium-based catalyst, for instance diphenylphosphinoferrocenepalladium dichloride.

A Suzuki type palladium coupling between compound 21 and compounds 3 and 1 (selected from an aryl bromide, iodide, chloride or triflate) allows the compounds having the aryl-aryl sequence 7 and 9, respectively, to be obtained.

A Suzuki palladium coupling between compound 22 and compounds 3 and 1 (selected from aryl bromide, iodide, chloride or triflate) allows compounds having the aryl-aryl sequence 8 and 11, respectively, to be obtained.

The compounds according to the invention show modulatory properties on receptors of PPAR type. This activity on the PPARα, δ and γ receptors is measured in a transactivation test and quantified via the dissociation constant Kdapp (apparent), as described in Example 6.

The preferred compounds of the present invention have a dissociation constant of less than or equal to 5,000 nM and advantageously less than or equal to 1,000 nM.

Preferably, the compounds are modulators of receptors of specific PPARγ type, i.e., they have a ratio between the Kdapp for the PPARα and PPARδ receptors, and the Kdapp for the PPARγ receptors, of greater than or equal to 10. Preferably, this ratio PPARγ/PPARα or PPARδ/PPARγ is greater than or equal to 50 and more advantageously greater than or equal to 100.

The present invention also features administration of the compounds of formula (I) as medicaments.

The present invention also features formulation of the compounds of formula (I) into compositions for regulating and/or restoring skin lipid metabolism.

The compounds according to the invention are also particularly useful in the following fields of treatments, whether regime or regimen:

1) for treating dermatological complaints, conditions or afflictions associated with a keratinization disorder relating to differentiation and to proliferation, in particular for treating common acne, comedones, polymorphs, rosacea, nodulocystic acne, acne conglobata, senile acne and secondary acne such as solar, medicinal or occupational acne, 2) for treating other types of keratinization disorders, in particular ichthyosis, ichthyosiform conditions, Darier's disease, palmoplantar keratoderma, leukoplakia and leukoplakiform conditions, and cutaneous or mucous (oral) lichen, 3) for treating other dermatological complaints, conditions or afflictions with an inflammatory immuno-allergic component, with or without a cellular proliferation disorder, and in particular all forms of psoriasis, whether cutaneous, mucous or ungual psoriasis, and even psoriatic arthritis, or alternatively cutaneous atopy such as eczema, or respiratory atopy or gingival hypertrophy, 4) for treating all dermal or epidermal proliferations, whether benign or malignant, whether or not of viral origin, such as common warts, flat warts and epidermodysplasia verruciformis, oral or florid papillomatoses, T lymphoma and proliferations which may be induced by ultraviolet light, in particular in the case of basal cell and spinocellular epithelioma, and also any precancerous skin lesion such as keratoacanthomas, 5) for treating other dermatological disorders, conditions or afflictions such as immune dermatitides, such as lupus erythematosus, bullous immune diseases and collagen diseases, such as scleroderma, 6) in the treatment of dermatological or systemic conditions having an immunological component, 7) in the treatment of skin disorders due to exposure to UV radiation, and also for repairing or combating aging of the skin, whether light-induced or chronological aging, or for reducing actinic keratoses and pigmentations, or any pathology associated with chronological or actinic aging, such as xerosis, 8) for combating sebaceous function disorders such as the hyperseborrhoea of acne, simple seborrhoea or seborrhoeic dermatitis, 9) for preventing or treating cicatrization disorders or for preventing or repairing stretch marks, 10) in the treatment of pigmentation disorders, such as hyperpigmentation, melasma, hypopigmentation or vitiligo, 11) in the treatment of lipid metabolism complaints, conditions or afflictions such as obesity, hyperlipidaemia, non-insulin-dependent diabetes or syndrome X, 12) in the treatment of inflammatory complaints, conditions or afflictions such as arthritis, 13) in the treatment or prevention of cancerous or precancerous conditions, 14) in the prevention or treatment of alopecia of various origins, in particular alopecia caused by chemotherapy or radiation, 15) in the treatment of immune system disorders, such as asthma, type I sugar diabetes, multiple sclerosis or other selective dysfunctions of the immune system, or 16) in the treatment of complaints, conditions or afflictions of the cardiovascular system, such as arteriosclerosis or hypertension.

The present invention also features pharmaceutical/cosmetic compositions comprising, formulated into a physiologically acceptable medium, at least one compound of formula (I) as defined above.

The compositions of this invention may be administered enterally, parenterally, topically or ocularly. The pharmaceutical composition is preferably packaged in a form that is suitable for topical application.

Via the enteral route, the composition, more particularly the pharmaceutical composition, may be in the form of tablets, gel capsules, sugar-coated tablets, syrups, suspensions, solutions, powders, granules, emulsions or lipid or polymer vesicles or nanospheres or microspheres to allow controlled release. Via the parenteral route, the composition may be in the form of solutions or suspensions for infusion or for injection.

The compounds according to the invention are generally administered at a daily dose of about 0.001 mg/kg to 100 mg/kg of body weight in 1 to 3 dosage intakes.

The compounds are administered systemically at a concentration generally of from 0.001% to 10% by weight and preferably from 0.01% to 1% by weight relative to the weight of the composition.

Via the topical route, the pharmaceutical composition according to the invention is more particularly intended for treating the skin and mucous membranes and may be in the form of ointments, creams, milks, salves, powders, impregnated pads, syndets, solutions, gels, sprays, foams, suspensions, stick lotions, shampoos or washing bases. It may also be in the form of suspensions of lipid or polymer vesicles or nanospheres or microspheres or polymer patches and hydrogels to allow controlled release. This topical-route composition may be in anhydrous form, in aqueous form or in the form of an emulsion.

The compounds are administered topically at a concentration generally of from 0.001% to 10% by weight, preferably from 0.01% to 1% by weight relative to the total weight of the composition.

The compounds of formula (I) according to the invention also find an application in the cosmetic field, in particular in body and hair hygiene and more particularly for regulating and/or restoring skin lipid metabolism.

This invention therefore also features the cosmetic application of a composition comprising, in a physiologically acceptable support, at least one of the compounds of formula (I) for body or hair hygiene.

The cosmetic compositions according to the invention containing, in a cosmetically acceptable support, at least one compound of formula (I) or an optical or geometrical isomer thereof or a salt thereof, may usually be in the form of a cream, a milk, a lotion, a gel, suspensions of lipid or polymer vesicles or nanospheres or microspheres, impregnated pads, solutions, sprays, foams, sticks, soaps, shampoos or washing bases.

The concentration of compound of formula (I) in the cosmetic composition is from 0.0001% to 2% by weight relative to the total weight of the composition.

The pharmaceutical and cosmetic compositions as described above may also contain inert or even pharmacodynamically active additives as regards the pharmaceutical compositions, or combinations of these additives, and especially:

wetting agents;
flavor enhancers;
preserving agents such as para-hydroxybenzoic acid esters;
stabilizers;
humidity regulators;
pH regulators;
osmotic pressure modifiers;
emulsifiers;
UV-A and UV-B screening agents;
antioxidants, such as α-tocopherol, butylhydroxyanisole or butylhydroxytoluene, superoxide dismutase, ubiquinol or certain metal-chelating agents;
depigmenting agents such as hydroquinone, azelaic acid, caffeic acid or kojic acid;
emollients;
moisturizers, for instance glycerol, PEG 400, thiamorpholinone and derivatives thereof, or urea;
anti-seborrhoeic or anti-acne agents, such as S-carboxymethylcysteine, S-benzylcysteamine, salts thereof or derivatives thereof, or benzoyl peroxide;
antibiotics, for instance erythromycin and its esters, neomycin, clindamycin and its esters, and tetracyclines;

anti-fungal agents such as ketoconazole or polymethylene-4,5-isothiazolidones-3;

agents for promoting regrowth of the hair, for instance Minoxidil (2,4-diamino-6-piperidinopyrimidine 3-oxide) and its derivatives, Diazoxide (7-chloro-3-methyl-1,2,4-benzothiadiazine 1,1-dioxide) and Phenyloin (5,4-diphenylimidazolidine-2,4-dione);

non-steroidal anti-inflammatory agents;

carotenoids, and especially β-carotene;

anti-psoriatic agents such as anthralin and its derivatives;

eicosa-5,8,11,14-tetraynoic acid and eicosa-5,8,11-triynoic acid, and esters and amides thereof;

retinoids, i.e., RAR or RXR receptor ligands, which may be natural or synthetic;

corticosteroids or oestrogens;

α-hydroxy acids and α-keto acids or derivatives thereof, such as lactic acid, malic acid, citric acid, glycolic acid, mandelic acid, tartaric acid, glyceric acid or ascorbic acid, and also the salts, amides or esters thereof, or β-hydroxy acids or derivatives thereof, such as salicylic acid and the salts, amides or esters thereof;

ion-channel blockers such as potassium-channel blockers;

or alternatively, more particularly for the pharmaceutical compositions, in combination with medicinal products known to interfere with the immune system (for example cyclosporin, FK 506, glucocorticoids, monoclonal antibodies, cytokines or growth factors, etc.).

Of course, one skilled in this art will take care to select the optional compound(s) to be added to these compositions such that the advantageous properties intrinsically associated with the present invention are not, or are not substantially, adversely affected by the envisaged addition.

This invention also features a cosmetic regime or regimen for beautifying the skin, wherein a composition comprising at least one compound of formula (I) as defined above is applied to the skin. Regulation and/or restoration of the metabolism of the skin lipids makes it possible to obtain skin whose surface appearance is embellished.

In order to further illustrate the present invention and the advantages thereof, the following examples of specific active compounds are given, as are the biological activities of such compounds and specific formulations thereof, it being understood that same are intended only as illustrative and in nowise limitative. In said examples to follow, all parts and percentages are given by weight, unless otherwise indicated.

EXAMPLE 1

Synthesis of 3-(5-{3-[(methyloctanoylamino)methyl]phenyl}thiophen-2-yl)acrylic acid

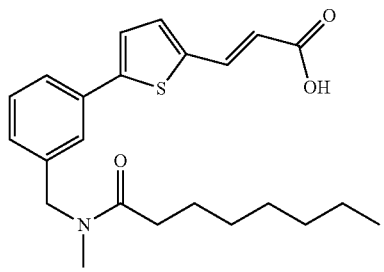 [SMILES: CCCCCCCC(=O)N(C)Cc1cccc(-c2ccc(/C=C/C(=O)O)s2)c1]

a. Preparation of N-methyloctanamide 25 g (0.37 mol) of methylamine hydrochloride are dissolved in 125 mL of dichloromethane, and 115 mL of triethylamine are then added. At 0° C., 70 mL (0.41 mol) of octanoyl chloride are added slowly. The reaction mixture is stirred for 3 hours at room temperature. The mixture is filtered and 100 ml of water are then added to the filtrate. The organic phase is separated out by settling, dried over sodium sulfate and evaporated. 61 g of N-methyloctanamide are obtained in quantitative yield.

b. Preparation of N-methyl-N-(3-bromobenzyl)octanamide 5 g (31.8 mmol) of N-methyloctanamide (1a) are added at 0° C. to a suspension of 1.4 g (35 mmol) of sodium hydride (60% in grease) in 60 mL of tetrahydrofuran. The reaction mixture is stirred for 30 minutes at room temperature and a solution of 8.9 g (35 mmol) of 3-bromobenzyl bromide in 15 mL of tetrahydrofuran is then added. The mixture is stirred for 16 hours at room temperature. The reaction is stopped by adding 100 mL of water and is then extracted with ethyl acetate. The organic phases are combined and dried over sodium sulfate. The solvents are evaporated off and the residue is then chromatographed on silica gel (75/25 heptane/ethyl acetate). 7.4 g of N-methyl-N-(3-bromobenzyl)octanamide are obtained. Yield=71%.

c. Preparation of octanoylmethyl-[3-(4,4,5,5-tetramethyl-[1,3,2]dioxaborolan-2-yl)benzyl]amide g (3.98 mmol, 1.3 eq) of pinacoldiborane is added to a mixture of 1.0 g (3.06 mmol, 1 eq) of N-methyl-N-(3-bromobenzyl) octanamide and 900 mg (9.18 mmol, 3 eq) of potassium acetate, in the presence of 111 mg (0.15 mmol, 5 mol %) of diphenylphosphinoferrocenepalladium dichloride (PdCl₂dppf) in 10 mL of dimethylformamide. The mixture is stirred for 2 hours at 80° C. The reaction is stopped by adding 20 ml of water and is then extracted with ethyl acetate. The organic phases are combined and dried over sodium sulfate. The solvents are evaporated off and the residue is then chromatographed on silica gel (80/20 heptane/ethyl acetate). 1.0 g of octanoylmethyl-[3-(4,4,5,5-tetramethyl[1,3,2]dioxaborolan-2-yl)benzyl]amide is obtained in the form of an oil. Yield=88%.

f. Preparation of methyl 3-(5-bromothiophen-2-yl)acrylate 4.2 g (12.5 mmol, 1.2 eq) of methyl triphenylphosphoranylideneacetate are added to a solution of 2.0 g (10.4 mmol, 1.0 eq) of 5-bromothiophene-2-carbaldehyde in 15 mL of toluene. The reaction mixture is stirred for 1 hour at 80° C. The reaction is stopped by adding 20 ml of water and is then extracted with ethyl acetate. The organic phases are combined and dried over sodium sulfate. The solvents are evaporated off and the residue is then chromatographed on silica gel (80/20 heptane/ethyl acetate). 2.1 g of methyl 3-(5-bromothiophen-2-yl)acrylate are obtained. Yield=82%.

g. Preparation of methyl 3-(5-{3-[(methyloctanoylamino)methyl]phenyl}thiophen-2-yl)acrylate 200 mg (0.81 mmol, 1.0 eq) of methyl 3-(5-bromothiophen-2-yl)acrylate and 334 mg (0.89 mmol, 1.1 eq) of octanoylmethyl-[3-(4,4,5,5-tetramethyl[1,3,2]dioxaborolan-2-yl)benzyl]amide are dissolved in 5 ml of a 5/1 mixture of dimethylformamide and of 2M potassium phosphate solution. 93 mg (0.08 mmol, 10 mol %) of tetrakis(triphenylphosphine)palladium are added and the reaction mixture is then stirred for 2 hours at 80° C. The reaction is stopped by adding 30 mL of water and is then extracted with ethyl acetate. The organic phases are combined and dried over sodium sulfate. The solvents are evaporated off and the residue is then chromatographed on silica gel (80/20 to 60/40 heptane/ethyl acetate). 220 mg of methyl 3-(5-{3-[(methyloctanoylamino)methyl]phenyl}thiophen-2-yl)acrylate are obtained. Yield=65%.

h. Synthesis of 3-(5-{3-[(methyloctanoylamino)methyl]phenyl}thiophen-2-yl)acrylic acid 212 mg (5.3 mmol, 10 eq) of sodium hydroxide are added to a solution of 220 mg (0.53 mmol, 1 eq) of methyl 3-(5-{3-[(methyloctanoylamino)methyl]phenyl}thiophen-2-yl)acrylate in 4 ml of 9/1 tetrahydrofuran/methanol. The reaction mixture is stirred for two hours at room temperature. The reaction is stopped by adding 20 ml of water and 3 ml of acetic acid and is then extracted with ethyl acetate. The organic phases are combined and dried over sodium sulfate. The solvents are evaporated off and the residue is then chromatographed on silica gel (90/10 dichloromethane/methanol). The oil obtained is crystallized from pentane. 155 mg of 3-(5-{3-[(methyloctanoylamino)methyl]phenyl}thiophen-2-yl)acrylic acid are obtained. Yield=73%. m.p.=102-104° C.

$^1$H NMR (CDCl$_3$, 400 MHz): 0.88 (m, 3H); 1.31 (m, 8H); 1.72 (m, 2H); 2.42 (m, 2H); 2.98&3.00 (2s(rotamers), 3H); 4.60&4.66 (2s(rotamers), 2H); 6.24&6.26 (2d(rotamers), J=15.6 Hz, 1H); 7.16-7.56 (m, 6H); 7.86 (2d(rotamers), J=15.6 Hz, 1H).

EXAMPLE 2

Synthesis of 3-(5-{3-[(methyloctanoylamino)methyl]phenyl}thiophen-2-yl)propanoic acid

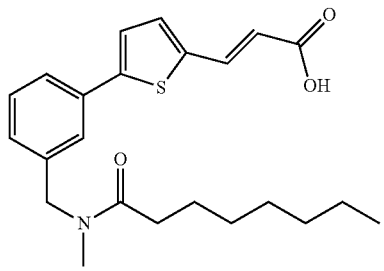 [SMILES: CCCCCCCC(=O)N(C)Cc1cccc(-c2ccc(/C=C/C(=O)O)s2)c1]

A solution of 80 mg (0.20 mmol, 1 eq) of 3-(5-{3-[(methyloctanoylamino)methyl]phenyl}thiophen-2-yl)acrylic acid (prepared as in 1 h) in 2 mL of methanol is stirred for 2 hours at room temperature in the presence of 50 mg of 10% Pd/C under a hydrogen atmosphere. The palladium is filtered off and the solvents are then evaporated off. The residue is crystallized from pentane/dichloromethane. 71 mg of 3-(5-{3-[(methyloctanoylamino)methyl]phenyl}thiophen-2-yl)propanoic acid are obtained. Yield=89%. m.p.=67-68° C.

$^1$H NMR (CDCl$_3$, 400 MHz): 0.88 (m, 3H); 1.28 (m, 8H); 1.70 (m, 2H); 2.41 (m, 2H); 2.78 (m, 2H); 2.96&2.98 (2s(rotamers), 3H); 3.18 (m, 2H); 4.57&4.63 (2s(rotamers), 2H); 6.82 (m, 1H); 7.05-7.14 (m, 2H); 7.28-7.48 (m, 3H).

EXAMPLE 3

Synthesis of 3-(5-{3-[(methyloctanoylamino)methyl]phenyl}furan-2-yl)acrylic acid

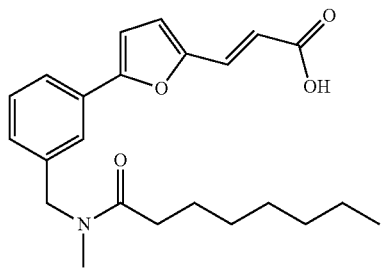 [SMILES: CCCCCCCC(=O)N(C)Cc1cccc(-c2ccc(/C=C/C(=O)O)o2)c1]

a. Preparation of methyl 3-(5-bromofuran-2-yl)acrylate 4.58 g (13.7 mmol, 1.2 eq) of methyl triphenylphosphoranylideneacetate are added to a solution of 2.0 g (11.4 mmol, 1.0 eq) of 5-bromofuran-2-carbaldehyde in 15 mL of toluene. The reaction mixture is stirred for 1 hour at 80° C. The reaction is stopped by adding 20 ml of water and is then extracted with ethyl acetate. The organic phases are combined and dried over sodium sulfate. The solvents are evaporated off and the residue is then chromatographed on silica gel (80/20 heptane/ethyl acetate). 2.0 g of methyl 3-(5-bromofuran-2-yl)acrylate are obtained. Yield=77%.

b. Preparation of methyl 3-(5-{3-[(methyloctanoylamino)methyl]phenyl}furan-2-yl)acrylate 278 mg (1.20 mmol, 1.5 eq) of methyl 3-(5-bromofuran-2-yl)acrylate and 300 mg (0.80 mmol, 1.0 eq) of octanoylmethyl-[3-(4,4,5,5-tetramethyl[1,3,2]dioxaborolan-2-yl)benzyl]amide (prepared as in 1e) are dissolved in 5 ml of a 5/1 mixture of dimethylformamide and of 2M potassium phosphate solution. 46 mg (0.04 mmol, 5 mol %) of tetrakis(triphenylphosphine)palladium are added and the reaction mixture is then stirred for 2 hours at 80° C. The reaction is stopped by adding 30 ml of water and is then extracted with ethyl acetate. The organic phases are combined and dried over sodium sulfate. The solvents are evaporated off and the residue is then chromatographed on silica gel (80/20 to 60/40 heptane/ethyl acetate). 250 mg of methyl 3-(5-{3-[(methyloctanoylamino)methyl]phenyl}furan-2-yl)acrylate are obtained. Yield=78%.

c. Synthesis of 3-(5-{3-[(methyloctanoylamino)methyl]phenyl}furan-2-yl)acrylic acid 300 mg (7.5 mmol, 12 eq) of sodium hydroxide are added to a solution of 250 mg (0.63 mmol, 1 eq) of 3-(5-{3-[(methyloctanoylamino)methyl]phenyl}furan-2-yl)acrylate in 4 mL of 9/1 tetrahydrofuran/methanol. The reaction mixture is stirred for two hours at room temperature. The reaction is stopped by adding 20 ml of water and 3 ml of acetic acid and is then extracted with ethyl acetate. The organic phases are combined and dried over sodium sulfate. The solvents are evaporated off and the residue is then chromatographed on silica gel (90/10 dichloromethane/methanol). The oil obtained is crystallized from pentane. 140 mg of 3-(5-{3-[(methyloctanoylamino)methyl]phenyl}furan-2-yl)acrylic acid are obtained. Yield=58%. m.p.=96-98° C.

$^1$H NMR (CDCl$_3$, 400 MHz): 0.88 (m, 3H); 1.28 (m, 8H); 1.71 (m, 2H); 2.42 (m, 2H); 2.98&3.00 (2s(rotamers), 3H); 4.61&4.67 (2s(rotamers), 2H); 6.43 (2d(rotamers), J=15.6 Hz, 1H); 6.76 (m, 2H); 7.18 (2d(rotamers), J=7.6 Hz, 1H); 7.37-7.69 (m, 4H).

EXAMPLE 4

Synthesis of 3-(4-{5-[(methyloctanoylamino)methyl]thiophen-3-yl}phenyl)acrylic acid

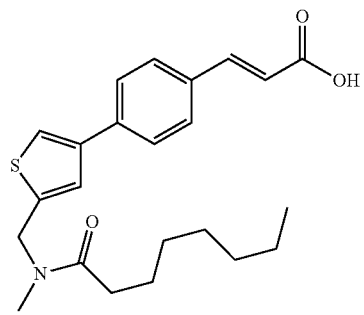 [SMILES: CCCCCCCC(=O)N(C)Cc1cc(-c2ccc(/C=C/C(=O)O)cc2)cs1]

a. Preparation of octanoyl(4-bromothiophen-2-ylmethyl)methylamide 880 mg (13 mmol, 5 eq) of methylamine hydrochloride and 500 mg (2.61 mmol, 1 eq) of 4-bromothiophene-2-carbaldehyde are dissolved in 5 ml of methanol in the presence of 2 g of anhydrous magnesium sulfate. The reaction mixture is stirred for 1 hour at room temperature. 327 mg (5.2 mmol, 2 eq) of sodium cyanoborohydride are added and the reaction mixture is stirred for 4 hours at room temperature. The reaction is stopped by adding 20 ml of water and is then extracted with ethyl acetate. The organic phases are combined and dried over sodium sulfate. The solvents are evaporated off and the residue is then dissolved in 4 ml of tetrahydrofuran in the presence of 0.5 mL of triethylamine. 0.45 mL (2.6 mmol, 1 eq) of octanoyl chloride is added and the reaction mixture is then stirred for 0.5 hour at room temperature. The reaction is stopped by adding 20 mL of water and is then extracted with ethyl acetate. The organic phases are combined and dried over sodium sulfate. The solvents are evaporated off and the residue is then chromatographed on silica gel (80/20 heptane/ethyl acetate). 300 mg of octanoyl(4-bromothiophen-2-ylmethyl)methylamide are obtained. Yield=35%.

b. Preparation of ethyl 3-[4-(4,4,5,5-tetramethyl[1,3,2]dioxaborolan-2-yl)phenyl]acrylate g (4.3 mmol, 1.1 eq) of pinacoldiborane are added to a mixture of 1.0 g (3.9 mmol, 1 eq) of ethyl 4-bromocinnamate and 1.1 g (11.7 mmol, 3 eq) of potassium acetate in the presence of 142 mg (0.19 mmol, 5 mol %) of diphenylphosphinoferrocenepalladium dichloride (PdCl$_2$dppf) in 10 mL of dimethylformamide. The mixture is stirred for 2 hours at 70° C. The reaction is stopped by adding 20 ml of water and is then extracted with ethyl acetate. The organic phases are combined and dried over sodium sulfate. The solvents are evaporated off and the residue is then chromatographed on silica gel (90/10 heptane/ethyl acetate). 1.15 g of ethyl 3-[4-(4,4,5,5-tetramethyl[1,3,2]dioxaborolan-2-yl)phenyl]acrylate are obtained in the form of an oil. Yield=98%.

c. Preparation of ethyl 3-(4-{5-[(methyloctanoylamino)methyl]thiophen-3-yl}phenyl)acrylate 300 mg (0.90 mmol, 1.0 eq) of octanoyl(4-bromothiophen-2-ylmethyl)methylamide and 326 mg (1.08 mmol, 1.2 eq) of ethyl 3-[4-(4,4,5,5-tetramethyl[1,3,2]dioxaborolan-2-yl)phenyl]acrylate are dissolved in 4 ml of a 5/1 mixture of dimethylformamide and of 2M potassium phosphate solution. 52 mg (0.04 mmol, 5 mol %) of tetrakis(triphenylphosphine)palladium are added and the reaction mixture is then stirred for 2 hours at 80° C. The reaction is stopped by adding 30 mL of water and is then extracted with ethyl acetate. The organic phases are combined and dried over sodium sulfate. The solvents are evaporated off and the residue is then chromatographed on silica gel (80/20 to 60/40 heptane/ethyl acetate). 250 mg of ethyl 3-(4-{5-[(methyloctanoylamino)methyl]thiophen-3-yl}phenyl)acrylate are obtained. Yield=65%.

d. Synthesis of 3-(4-{5-[methyloctanoylamino)methyl]thiophen-3-yl}phenyl)acrylic acid 230 mg (5.8 mmol, 10 eq) of sodium hydroxide are added to a solution of 250 mg (0.58 mmol, 1 eq) of ethyl 3-(4-{5-[(methyloctanoylamino)methyl]thiophen-3-yl}phenyl)acrylate in 4 mL of 9/1 tetrahydrofuran/methanol. The reaction mixture is stirred for 2 hours at room temperature. The reaction is stopped by adding 20 mL of water and 3 mL of acetic acid and is then extracted with ethyl acetate. The organic phases are combined and dried over sodium sulfate. The solvents are evaporated off and the residue is then chromatographed on silica gel (90/10 dichloromethane/methanol). The oil obtained is crystallized from pentane. 80 mg of 3-(4-{5-[(methyloctanoylamino)methyl]thiophen-3-yl}phenyl)acrylic acid are obtained. Yield=35%. m.p.=175° C.

$^1$H NMR (CDCl$_3$, 400 MHz): 0.88 (m, 3H); 1.33 (m, 8H); 1.70 (m, 2H); 2.38&2.48 (2t(rotamers), J=7.6 Hz, 2H); 3.05&3.06 (2s(rotamers), 3H); 4.71&4.76 (2s(rotamers), 2H); 6.47&6.49 (2d(rotamers), J=15.9 Hz, 1H); 6.76 (m, 2H); 7.28 (m, 1H); 7.44 (m, 1H); 7.60 (m, 4H); 7.80 (2d(rotamers), J=15.9 Hz, 1H).

EXAMPLE 5

Synthesis of 3-(4-{5-[(methyloctanoylamino)methyl]thiophen-3-yl}phenyl)propanoic acid

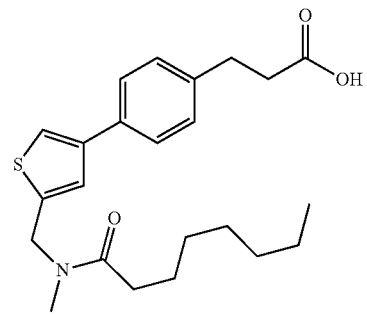 [SMILES: CCCCCCCC(=O)N(C)Cc1cc(-c2ccc(CCC(=O)O)cc2)cs1]

a. Preparation of ethyl 3-[4-(4,4,5,5-tetramethyl[1,3,2]dioxaborolan-2-yl)phenyl]propanoate A solution of 8 g (26.4 mmol) of ethyl 3-[4-(4,4,5,5-tetramethyl[1,3,2]dioxaborolan-2-yl)phenyl]acrylate in 30 mL of methanol is stirred for one hour at room temperature in the presence of 400 mg of 10% palladium-on-charcoal under a hydrogen atmosphere. The catalyst is filtered off and the solvents are then evaporated off. 7.8 g of ethyl 3-[4-(4,4,5,5-tetramethyl[1,3,2]dioxaborolan-2-yl)phenyl]propanoate are obtained. Yield=96%.

b. Preparation of ethyl 3-(4-{5-[(methyloctanoylamino)methyl]thiophen-3-yl}phenyl)propanoate 430 mg (1.29 mmol, 1 eq) of octanoyl(4-bromothiophen-2-ylmethyl)methylamide and 470 mg (1.55 mmol, 1.2 eq) of ethyl 3-[4-(4,4,5,5-tetramethyl[1,3,2]dioxaborolan-2-yl)phenyl]propanoate are dissolved in 4 ml of a 6/1 mixture of dimethylformamide and of 2M potassium phosphate solution. 15 mg (0.064 mmol, 5 mol %) of palladium acetate and 45 mg (0.129 mmol, 10 mol %) of dicyclohexyl 2-biphenylphosphine are added. The mixture is stirred for 2 hours at 90° C. The reaction is stopped by adding 30 mL of water and is then extracted with ethyl acetate. The organic phases are combined and dried over sodium sulfate. The solvents are evaporated off and the residue is then chromatographed on silica gel (80/20 to 70/30 heptane/ethyl acetate). 245 mg of ethyl 3-(4-{5-[(methyloctanoylamino)methyl]thiophen-3-yl}phenyl)propanoate are obtained. Yield=44%.

c. Synthesis of 3-(4-{5-[(methyloctanoylamino)methyl]thiophen-3-yl}phenyl)propanoic acid 100 mg (2.5 mmol, 4 eq) of sodium hydroxide are added to a solution of 245 mg (0.57 mmol, 1 eq) of ethyl 3-(4-{5-[(methyloctanoylamino)methyl]thiophen-3-yl}phenyl)propanoate in 4 mL of 9/1 tetrahydrofuran/methanol. The reaction mixture is stirred for two hours at room temperature. The reaction is stopped by adding 20 mL of water and 3 mL of acetic acid and is then extracted with ethyl acetate. The organic phases are combined and dried over sodium sulfate. The solvents are evaporated off and the residue is then chromatographed on silica gel (90/10 dichloromethane/methanol). The oil obtained is crystallized from pentane. 85 mg of 3-(4-{5-[(methyloctanoylamino)methyl]thiophen-3-yl}phenyl)propanoic acid are obtained. Yield=37%.

$^1$H NMR (CDCl$_3$, 400 MHz): 0.89 (m, 3H); 1.32 (m, 8H); 1.70 (m, 2H); 2.37&2.48 (2t(rotamers), J=7.2 Hz, 2H); 2.71 (t, 2H, J=7.6 Hz); 2.99 (m, 2H); 3.02 (s, 3H); 4.74&4.69 (2s(rotamers), 2H); 7.18-7.34 (m, 4H); 7.50 (d, J=3.2 Hz, 2H).

EXAMPLE 6

Synthesis of 3-{4-[6-(3-heptyl-1-methylureido)pyrid-2-yl]phenyl}propanoic acid

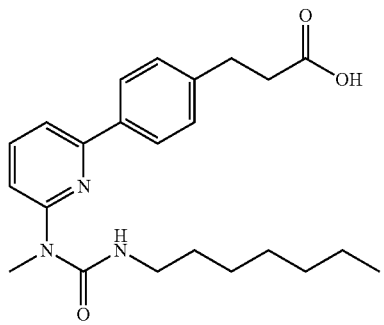 [SMILES: CCCCCCCNC(=O)N(C)c1cccc(-c2ccc(CCC(=O)O)cc2)n1]

a. Preparation of tert-butyl (6-bromopyrid-2-yl)carbamate 62 g (284 mmol) of di-tert-butyl dicarbonate diluted in 200 ml of dichloromethane are added dropwise to a solution of 49.2 g (284 mmol) of 2-amino-6-bromopyridine, 43.4 ml (312 mmol) of triethylamine and 3.5 g (28.4 mmol) of 4-dimethylaminopyridine in 400 ml of dichloromethane. The reaction medium is stirred at room temperature for 18 hours. After addition of water and extraction with dichloromethane, the organic phase is dried over magnesium sulfate, filtered and evaporated. The residue obtained is purified by chromatography on a column of silica eluted with a 95/5 heptane/ethyl acetate mixture. 39 g (50%) of tert-butyl (6-bromopyrid-2-yl)carbamate are obtained in the form of a white solid.

b. Preparation of tert-butyl 6-bromopyrid-2-yl-N-methylcarbamate

To a solution of 39 g (14.3 mmol) of tert-butyl (6-bromopyrid-2-yl)carbamate in 400 ml of dimethylformamide are added portionwise 6.9 g (17.2 mmol) of 60% sodium hydride in oil. After stirring for 20 minutes at room temperature, 17.8 ml (28.6 mmol) of methyl iodide are added dropwise. The reaction medium is stirred at room temperature for 18 hours, taken up in water and extracted with ethyl acetate. The organic phase is dried over magnesium sulfate, filtered and evaporated.

c. Preparation of ethyl 3-{4-[6-(tert-butoxycarbonylmethylamino)pyrid-2-yl]phenyl}acrylate 1.25 g (4.13 mmol, 1.2 eq) of ethyl 3-[4-(4,4,5,5-tetramethyl[1,3,2]dioxaborolan-2-yl)phenyl]acrylate and 1.0 g (3.48 mmol, 1 eq) of tert-butyl (6-bromopyrid-2-yl)-methylcarbamate are dissolved in 15 ml of a 6/1 mixture of dimethylformamide and of 2M potassium phosphate solution. 200 mg (0.173 mmol, 5 mol %) of tetrakis(triphenylphosphine)palladium are added. The mixture is stirred for 3 hours at 90° C. The reaction is stopped by adding 30 mL of water and is then extracted with ethyl acetate. The organic phases are combined and dried over sodium sulfate. The solvents are evaporated off and the residue is then chromatographed on silica gel (80/20 to 70/30 heptane/ethyl acetate). 850 mg of ethyl 3-{-4-[6-(tert-butoxycarbonylmethylamino)pyrid-2-yl]phenyl}acrylate are obtained. Yield=64%.

d. Preparation of ethyl 3-{4-[6-(3-heptyl-1-methylureido)pyrid-2-yl]phenyl}acrylate 300 mg (0.78 mmol) of ethyl 3-{4-[6-(tert-butoxycarbonylmethylamino)pyrid-2-yl]phenyl}acrylate are dissolved in 5 mL of dichloromethane. 2 mL of trifluoroacetic acid are added. The reaction mixture is stirred for 3 hours at room temperature. The reaction is stopped by adding 30 mL of saturated sodium hydrogen carbonate solution and is then extracted with ethyl acetate. The organic phases are combined and dried over sodium sulfate. The solvents are evaporated off and the oil obtained is then dissolved in 5 ml of dichloromethane in the presence of 1 ml of triethylamine. 630 µL (3.9 mmol, 5 eq) of heptyl isocyanate are added along with 100 mg of dimethylaminopyridine. The reaction mixture is stirred for 16 hours at reflux. The reaction is stopped by adding 30 mL of water and is then extracted with ethyl acetate. The organic phases are combined and dried over sodium sulfate. The solvents are evaporated off and the residue is then chromatographed on silica gel (80/20 to 70/30 heptane/ethyl acetate). 170 mg of ethyl 3-{4-[6-(3-heptyl-1-methylureido)pyrid-2-yl]phenyl}acrylate are obtained. Yield=51%.

e. Synthesis of 3-{4-[6-(3-heptyl-1-methylureido)pyrid-2-yl]phenyl}propanoic acid 170 mg (0.4 mmol) of ethyl 3-{4-[6-(3-heptyl-1-methylureido)pyrid-2-yl]phenyl}acrylate are dissolved in 5 ml of methanol. 50 mg of 10% palladium-on-charcoal are added. The reaction mixture is stirred for 3 hours at room temperature under a hydrogen atmosphere. The catalyst is filtered off and the solvents are then evaporated off and the oil obtained is used directly in the following reaction. 170 mg of sodium hydroxide are added to the solution of ethyl 3-{4-[6-(3-heptyl-1-methylureido)pyrid-2-yl]phenyl}propanoate in 5 ml of 9/1 tetrahydrofuran/methanol. The reaction mixture is stirred for two hours at room temperature. The reaction is stopped by adding 20 mL of water and 3 mL of acetic acid and is then extracted with ethyl acetate. The organic phases are combined and dried over sodium sulfate. The solvents are evaporated off and the residue is then chromatographed on silica gel (7/3 to 1/1 heptane/EtOAc). 110 mg of 3-{4-[6-(3-heptyl-1-methylureido)pyrid-2-yl]phenyl}propanoic acid are obtained. Yield=69% over two steps. m.p.=108° C.

$^1$H NMR (CDCl$_3$, 400 MHz): 0.87 (t, J=7.0 Hz, 3H); 1.20-1.36 (m, 8H); 1.61 (m, 2H); 2.76 (t, J=7.7 Hz, 2H); 3.06 (t, 2H, J=7.7 Hz); 3.38 (q, J=5.5 Hz, 2H); 3.47 (s, 3H); 6.94 (d, J=8.4 Hz, 1H); 7.35 (m, 3H); 7.76 (t, J=7.8 Hz, 1H); 7.81 (d, J=8.0 Hz, 2H); 10.48 (s, 1H).

EXAMPLE 7

Synthesis of 3-{6-[3-(3-heptyl-1-methylureido)phenyl]pyrid-2-yl}propanoic acid

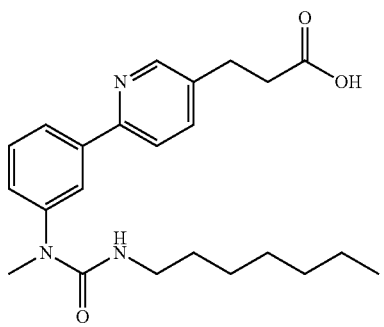 [SMILES: CCCCCCCNC(=O)N(C)c1cccc(-c2ccc(CCC(=O)O)cn2)c1]

a. Preparation of tert-butyl (3-bromophenyl)carbamate

To a mixture of 94 g (549 mmol) of 3-bromoaniline and 1 l of dichloromethane are added portionwise, at room temperature, 120 g (549 mmol) of di-tert-butyl dicarbonate. After stirring for 18 hours, the reaction medium is poured into ice-water and then extracted with dichloromethane. The organic phase is separated out by settling of the phases, dried over magnesium sulfate and evaporated. 138 g of tert-butyl (3-bromophenyl)carbamate are obtained in a yield of 98%.

b. Preparation of tert-butyl (3-bromophenyl)-N-methylcarbamate

To a solution of 114 g (447 mmol) of tert-butyl (3-bromophenyl)carbamate in 800 ml of DMF are added portionwise 19 g (475 mmol) of sodium hydride (60% in oil) and the reaction medium is stirred until the evolution of gas has ceased. 29.3 ml (470 mmol) of methyl iodide are added dropwise and stirring is continued for 18 hours. The reaction medium is poured into ice-water and extracted with ethyl acetate. The organic phase is separated out by settling of the phases, dried over magnesium sulfate and evaporated. 115 g of tert-butyl (3-bromophenyl)-N-methylcarbamate are obtained in a yield of 95%.

c. Preparation of (3-bromophenyl)methylamine 5 ml of trifluoromethanesulfonic acid are added to a solution of 3.6 g (12.7 mmol) of tert-butyl (3-bromophenyl)-N-methylcarbamate in 15 mL of dichloromethane. The reaction medium is stirred for 1 hour at room temperature (RT). The reaction is stopped by adding 50 ml of saturated sodium hydrogen carbonate solution and then extracted with ethyl acetate. The solvents are evaporated off and the residue is then chromatographed on silica gel, eluting with 1/1 heptane/ethyl acetate. 2.14 g of oil are obtained. 90% yield.

d. Preparation of N-methyl-3-aminophenylboronic acid 37.6 g (202 mmol, 1 eq) of (3-bromophenyl)methylamine (obtained as in 1c) are dissolved in 300 mL of tetrahydrofuran. The reaction mixture is cooled to −70° C. and 166 mL (242 mmol, 1.2 eq) of 1.5 M methyllithium are then added slowly, while keeping the temperature at −70° C. The reaction mixture is stirred for 1 hour at −70° C. 306 mL (444 mmol, 2.2 eq) of 1.46 M tert-butyllithium are added, while keeping the temperature at −70° C. The reaction mixture is stirred for 45 minutes at −70° C. 103.5 ml (808 mmol, 4 eq) of trimethyl borate are added at −65° C. and the reaction mixture is then warmed to room temperature. The reaction is stopped by adding 1 L of 1N hydrochloric acid. The pH is adjusted to pH 5 and the reaction medium is then extracted with n-butanol. The organic phases are combined and dried over sodium sulfate. The solvents are evaporated off and the residue is then chromatographed on silica gel (70/30 heptane/ethyl acetate). 11.3 g of N-methyl-3-aminophenylboronic acid are obtained. Yield=40%.

e. Preparation of [3-(5-bromopyrid-2-yl)phenyl]methylamine 2.2 g (9.5 mmol, 1.2 eq) of 2,5-dibromopyridine are dissolved in 3 mL of an 8/2 mixture of dimethylformamide/2M potassium phosphate. 1.2 g (7.9 mmol, 1 eq) of N-methyl-3-aminophenylboronic acid are added along with 456 mg (0.39 mmol, 5 mol %) of tetrakis(triphenylphosphine)palladium. The mixture is stirred for 3 hours at 90° C. The reaction is stopped by adding 30 mL of water and is then extracted with ethyl acetate. The organic phases are combined and dried over sodium sulfate. The solvents are evaporated and the residue is then chromatographed on silica gel (80/20 to 70/30 heptane/ethyl acetate). 1.07 g of [3-(5-bromopyrid-2-yl)phenyl]methylamine are obtained. Yield=52%.

f. Preparation of tert-butyl [3-(5-bromopyrid-2-yl)phenyl]methylcarbamate 1.07 g (4 mmol, 1 eq) of [3-(5-bromopyrid-2-yl)phenyl]methylamine are dissolved in 10 mL of dichloromethane in the presence of 1 mL of triethylamine and 200 mg of dimethylaminopyridine. 1.7 g (8 mmol, 2 eq) of tert-butyl dicarbonate are added and the reaction mixture is stirred overnight at 40° C. The reaction is stopped by adding 30 ml of water and is then extracted with ethyl acetate. The organic phases are combined and dried over sodium sulfate. The solvents are evaporated off and the residue is then chromatographed on silica gel (70/30 heptane/ethyl acetate). 1.18 g of tert-butyl [3-(5-bromopyrid-2-yl)phenyl}methylcarbamate are obtained. Yield=81%.

g. Preparation of ethyl 3-{6-[3-(tert-butoxycarbonylmethylamino)phenyl]pyrid-3-yl}acrylate 1.18 g of tert-butyl [3-(5-bromopyrid-2-yl) phenyl}methylcarbamate (3.25 mmol, 1 eq) are dissolved in 10 mL of dimethylformamide and 1 ml of triethylamine. 110 mg (0.48 mmol, 15%) of palladium acetate and 296 mg (0.96 mmol, 30%) of o-tolylphosphine are added, along with 1 mL of ethyl acrylate. The reaction mixture is stirred overnight at 80° C. The reaction is stopped by adding 30 ml of water and is then extracted with ethyl acetate. The organic phases are combined and dried over sodium sulfate. The solvents are evaporated off and the residue is then chromatographed on silica gel (70/30 heptane/ethyl acetate). 852 mg of ethyl 3-{6-[3-(tert-butoxycarbonylmethylamino)phenyl}pyrid-3-yl] acrylate are obtained. Yield=68%.

h. Preparation of ethyl 3-[6-(3-methylaminophenyl)pyrid-3-yl]propanoate

A solution of 852 mg (2.23 mmol) of ethyl 3-{6-[3-(tert-butoxycarbonylmethylamino)phenyl}pyrid-3-yl}acrylate in 10 mL of methanol is stirred for 4 hours at room temperature in the presence of 100 mg of 10% palladium-on-charcoal under a hydrogen atmosphere. The catalyst is filtered off and the solvents are then evaporated off. The oil obtained is dissolved in 15 mL of dichloromethane. 2 mL of trifluoroacetic acid are added and the reaction mixture is stirred for 4 hours at room temperature. The reaction is stopped by adding 100 mL of saturated sodium hydrogen carbonate solution and is then extracted with ethyl acetate. The organic phases are combined and dried over sodium sulfate. The solvents are evaporated off and the residue is then chromatographed on silica gel (70/30 heptane/ethyl acetate). 710 mg of ethyl 3-[6-(3-methylaminophenyl)pyrid-3-yl]propanoate are obtained. Yield=68%.

i. Preparation of ethyl 3-{6-[3-(3-heptyl-1-methylureido) phenyl]pyrid-3-yl}propanoate 572 μL (3.5 mmol, 2 eq) of heptyl isocyanate are added to a solution of 500 mg (1.76 mmol, 1 eq) of ethyl 3-[6-(3-methylaminophenyl)pyrid-3-yl]propanoate in 10 mL of a 4/1 tetrahydrofuran/triethylamine mixture. The reaction mixture is stirred for 24 hours at 40° C. The reaction is stopped by adding 30 ml of water and is then extracted with ethyl acetate. The organic phases are combined and dried over sodium sulfate. The solvents are evaporated off and the residue is then chromatographed on silica gel (70/30 heptane/ethyl acetate). 488 mg of ethyl 3-{6-[3-(3-heptyl-1-methylureido)phenyl] pyrid-3-yl}propanoate are obtained. Yield=65%.

j. Synthesis of 3-{6-[3-(3-heptyl-1-methylureido)phenyl] pyrid-3-yl}propanoic acid 200 mg (5 mmol, 4 eq) of sodium hydroxide are added to a solution of 488 mg (1.14 mmol, 1 eq) of ethyl 3-{6-[3-(3-heptyl-1-methylureido)phenyl]pyrid-3-yl}propanoate in 6 mL of 9/1 tetrahydrofuran/methanol. The reaction mixture is stirred for 3 hours at room temperature. The reaction is stopped by adding 20 ml of water and 3 ml of acetic acid and is then extracted with ethyl acetate. The organic phases are combined and dried over sodium sulfate. The solvents are evaporated off and the residue is then chromatographed on silica gel (70/30 to 50/50 heptane/ethyl acetate). The oil obtained is crystallized from pentane. 442 mg of 3-{6-[3-(3-heptyl-1-methylureido)phenyl]pyrid-3-yl}propanoic acid are obtained. Yield=94%. m.p.=118° C.

$^1$H NMR (CDCl$_3$, 400 MHz): 0.85 (t, J=6.8 Hz, 3H); 1.25 (m, 8H); 1.40 (m, 2H); 2.74 (t, J=7.4 Hz, 2H); 3.05 (t, J=7.3 Hz, 2H); 3.17 (q, J=6.0 Hz, 2H); 3.32 (s, 3H); 4.42 (m, 1H); 7.29 (m, 1H); 7.52 (t, J=8.0 Hz, 1H); 7.66 (m, 2H); 7.86 (m, 2H); 8.63 (m, 1H).

EXAMPLE 8

Synthesis of 2-[4-(2-carboxyethyl)phenyl]-4-(3-heptyl-1-methylureido)pyridinium acetate

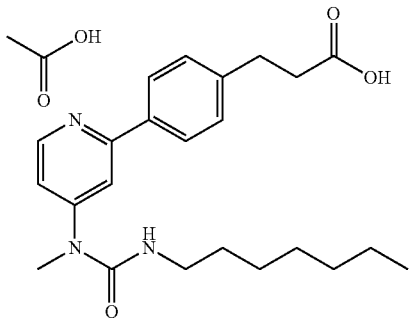

a. Preparation of tert-butyl (2-chloropyrid-4-yl)carbamate 1.69 g (7.78 mmol, 1 eq) of tert-butyl dicarbonate dissolved in 50 ml of dichloromethane, in the presence of 95 mg of dimethylaminopyridine, are added to a solution of 1 g (7.78 mmol, 1 eq) of 4-amino-2-chloropyridine in 30 mL of dichloromethane in the presence of 1.19 mL (1.19 mmol, 1.1 eq) of triethylamine. The reaction mixture is stirred overnight at room temperature. The reaction is stopped by adding 100 ml of water and is then extracted with dichloromethane. The organic phases are combined and dried over sodium sulfate. The solvents are evaporated off and the residue is then chromatographed on silica gel (70/30 to 50/50 heptane/ethyl acetate). The oil obtained is crystallized from pentane. 1.40 g of tert-butyl (2-chloropyrid-4-yl)carbamate are obtained. Yield=80%.

b. Preparation of tert-butyl (2-chloropyrid-4-yl)methylcarbamate

A solution of 17.5 g (76.7 mmol, 1 eq) dissolved in 100 ml of dimethylformamide is added to a suspension of 3.57 g (92 mmol, 1.2 eq) of sodium hydride in 100 mL of dimethylformamide at 0° C. The reaction mixture is stirred for 30 minutes at room temperature. 9.26 ml (148 mmol, 2 eq) of methyl iodide are added to the reaction mixture and the reaction medium is then stirred for 2 hours at room temperature. The reaction is stopped by adding 100 mL of water and is then extracted with ethyl acetate. The organic phases are combined and dried over sodium sulfate. The solvents are evaporated off. 18 g of tert-butyl (2-chloropyrid-4-yl)methylcarbamate are obtained. Yield=97%.

c. Preparation of ethyl 3-{4-[4-(tert-butoxycarbonylmethylamino)pyrid-2-yl]phenyl}propanoate 500 mg (2.06 mmol, 1 eq) of tert-butyl (2-chloropyrid-4-yl)methylcarbamate and 750 mg (2.47 mmol, 1.2 eq) of ethyl 3-[4-(4,4,5,5-tetramethyl[1,3,2]dioxaborolan-2-yl)phenyl]propanoate (obtained as in 5a) are dissolved in 10 mL of an 8/2 mixture of dimethylformamide/2M potassium phosphate. 23 mg (0.123 mmol, 5 mol %) of palladium acetate and 71 mg (0.24 mmol, 10 mol %) of dicyclohexyldiphenylphosphine are added. The mixture is stirred for 4 hours at 90° C. The reaction is stopped by adding 30 ml of water and is then extracted with ethyl acetate. The organic phases are combined and dried over sodium sulfate. The solvents are evaporated off and the residue is then chromatographed on silica gel (80/20 to 70/30 heptane/ethyl acetate). 415 mg of ethyl 3-{4-[4-(tert-butoxycarbonylmethylamino)pyrid-2-yl]phenyl}propanoate are obtained. Yield=52%.

d. Preparation of ethyl 3-[4-(4-methylaminopyrid-2-yl)phenyl]propanoate 415 mg (1.08 mmol, 1 eq) of ethyl 3-{4-[4-(tert-butoxycarbonylmethylamino)pyrid-2-yl]phenyl}propanoate are dissolved in 10 mL of dichloromethane. 3 mL of trifluoroacetic acid are added and the reaction mixture is stirred for 4 hours at room temperature. The reaction is stopped by adding 100 mL of saturated sodium hydrogen carbonate solution and is then extracted with ethyl acetate. The organic phases are combined and dried over sodium sulfate. The solvents are evaporated off. 270 mg of ethyl 3-[4-(4-methylaminopyrid-2-yl)phenyl]propanoate are obtained. Yield=88%.

e. Preparation of ethyl 3-{4-[4-(3-heptyl-1-methylureido)pyrid-2-yl]phenyl}propanoate 270 mg (0.63 mmol, 1 eq) of ethyl 3-[4-(4-methylaminopyrid-2-yl)phenyl]propanoate are mixed with 0.6 mL (3.7 mmol, 6 eq) of heptyl isocyanate and then irradiated in a microwave machine for 2 times 30 minutes, while keeping the temperature constant at 100° C. The reaction mixture is chromatographed on silica gel (90/10 heptane/ethyl acetate). 260 mg of ethyl 3-{4-[4-(3-heptyl-1-methylureido)pyrid-2-yl]phenyl}propanoate are obtained. Yield=64%.

f. Synthesis of 2-[4-(2-carboxyethyl)phenyl]-4-(3-heptyl-1-methylureido)pyridinium acetate 100 mg (2.5 mmol, 4 eq) of sodium hydroxide are added to a solution of 260 mg (0.61 mmol, 1 eq) of ethyl 3-{4-[4-(3-heptyl-1-methylureido)pyrid-2-yl]phenyl}propanoate in 5 ml of 9/1 tetrahydrofuran/methanol. The reaction mixture is stirred for two hours at room temperature. The reaction is stopped by adding 20 mL of water and 3 mL of acetic acid and is then extracted with ethyl acetate. The organic phases are combined and dried over sodium sulfate. The solvents are evaporated off and the residue is then crystallized from pentane. 143 mg of 2-[4-(2-carboxyethyl)phenyl]-4-(3-heptyl-1-methylureido)pyridinium acetate are obtained. Yield=59%. m.p.=71-73° C.

$^1$H NMR (CDCl$_3$, 400 MHz): 0.88 (t, J=7.2 Hz, 3H); 1.32 (m, 8H); 1.58 (m, 2H); 2.11 (s, 3H); 2.70 (t, J=6.9 Hz, 2H); 3.00 (t, J=6.9 Hz, 2H); 3.29 (q, J=6.3 Hz, 2H); 3.38 (s, 3H); 6.14 (m, 1H); 7.12 (d, J=5.6 Hz, 1H); 7.31 (d, J=7.6 Hz, 2H); 7.51 (s, 1H); 7.79 (d, J=7.6 Hz, 2H); 8.43 (d, J=5.5 Hz, 1H).

EXAMPLE 9

Synthesis of 3-{5-[3-(1-methyl-3-pentylureido)phenyl]pyrimidin-2-yl)acrylic acid

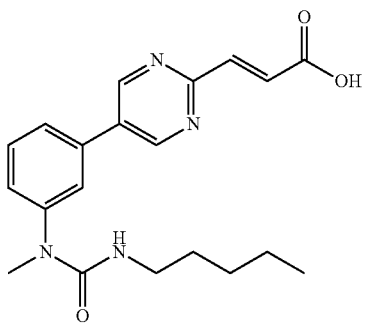 [SMILES: CCCCCNC(=O)N(C)c1cccc(-c2cnc(/C=C/C(=O)O)nc2)c1]

a. Preparation of 3-(N-methyl-N-tert-butoxycarbonyl)phenylboronic acid 18.5 ml (46.2 mmol, 1.3 eq) of 2.5M butyllithium in hexane are added to a solution of 10 g (34.9 mmol, 1 eq) of tert-butyl (3-bromophenyl)methylcarbamate (obtained as in 7b) in 25 mL of tetrahydrofuran cooled to –78° C. The reaction mixture is stirred for 30 minutes at –78° C. and 10 mL (41.9 mmol, 1.2 eq) of diisopropyl borate are then added dropwise. The reaction mixture is stirred at –78° C. for 2 hours. The reaction is stopped by adding 70 ml of 1N hydrochloric acid at –10° C., and is then extracted with ethyl acetate. The organic phases are combined and dried over sodium sulfate. The solvents are evaporated off. 9.17 g of 3-(N-methyl-N-tert-butoxycarbonyl)phenylboronic acid are obtained in a crude yield of 100%.

b. Preparation of tert-butyl [3-(2-bromopyrimidin-5-yl)phenyl]methylcarbamate 22 ml of 2M potassium carbonate (43.9 mmol, 2.5 eq) are added dropwise to a solution of 3-(N-methyl-N-tert-butoxycarbonyl)phenylboronic acid (5.3 g, 21.06 mmol, 1.2 eq) and 5-bromo-2-iodopyrimidine (5 g, 17.6 mmol, 1 eq) in 50 ml of diethyl ether. The reaction medium is degassed with nitrogen for 30 minutes and tetrakis(triphenylphosphine)palladium (1.01 g, 0.88 mmol, 0.05 eq) is then added. The reaction mixture is stirred overnight at 100° C. The reaction is stopped by adding water and is then extracted with ethyl acetate. The solvents are evaporated off and the residue is then chromatographed on silica gel (90/10 heptane/ethyl acetate). 1.87 g of tert-butyl [3-(2-bromopyrimidin-5-yl)phenyl]methylcarbamate are obtained in the form of a beige-colored solid in a yield of 30%.

c. Preparation of methyl 3-{5-[3-(tert-butoxycarbonylmethylamino)phenyl]pyrimidin-2-yl}acrylate 0.25 ml (2.75 mmol, 2 eq) of methyl acrylate, 9.3 mg (0.04 mmol, 0.3 eq) of palladium acetate and 25 mg (0.08 mmol, 0.06 eq) of tri-ortho-tolylphosphine are added to a solution of 0.5 g (1.37 mmol, 1 eq) of tert-butyl [3-(2-bromopyrimidin-5-yl)phenyl]methylcarbamate in 0.5 ml of dimethylformamide. The reaction mixture is heated at 80° C. overnight. The reaction is stopped by adding 20 ml of water and is then extracted with ethyl acetate. The organic phases are combined and dried over sodium sulfate. The solvents are evaporated off and the residue is then chromatographed on silica gel (95/5 heptane/ethyl acetate). 377.7 mg of methyl 3-{5-[3-(tert-butoxycarbonylmethylamino)phenyl]pyrimidin-2-yl}acrylate are obtained in the form of a beige-colored solid. Yield=75%.

d. Preparation of methyl 3-(3'-methylaminobiphenyl-4-yl)acrylate 0.16 ml (2.04 mmol, 5 eq) of trifluoroacetic acid is added to a solution of 151 mg (0.4 mmol, 1 eq) of methyl 3-{5'-[3-(tert-butoxycarbonylmethylamino)phenyl]pyrimidin-2-yl}acrylate in 3 ml of dichloromethane. The reaction mixture is stirred for eight hours at room temperature. The reaction is stopped by adding aqueous ammonia solution and is then extracted with ethyl acetate. The organic phases are combined and dried over sodium sulfate. The solvents are evaporated off and the residue is then taken up in heptane. 71.6 mg of methyl 3-(3'-methylaminobiphenyl-4-yl)acrylate are obtained in the form of a yellow solid. Yield=65%.

e. Preparation of methyl 3-(5-[3-(1-methyl-3-pentylureido)phenyl]pyrimidine-2-acrylate 22 μL (0.53 mmol, 1 eq) of pentyl isocyanate are added dropwise to a solution of 71.6 mg (0.27 mmol, 1 eq) of methyl 3-[5-(3-methylaminophenyl)pyrimidin-2-yl]acrylate and 22 μL of triethylamine in 2 mL of dichloromethane. The reaction mixture is stirred for 2 days at room temperature. The reaction is stopped by adding 10 ml of water and is then extracted with ethyl acetate. The organic phases are combined and dried over sodium sulfate. The solvents are evaporated off and the residue is then chromatographed on silica gel (70/30 heptane/ethyl acetate). 37.6 mg of methyl 3-{5-[3-(1-methyl-3-pentylureido)phenyl]pyrimidine-2-acrylate are obtained in the form of white crystals. Yield=38%.

f. Synthesis of 3-{5-[3-(1-methyl-3-pentylureido)phenyl]pyrimidin-2-yl}acrylic acid 10 mg (242.5 μmol, 2.5 eq) of sodium hydroxide pellets are added to a solution of 37.6 mg (97 μmol, 1 eq) of 3-{5-[3-(1-methyl-3-pentylureido)phenyl]pyrimidine-2-acrylate in 2 ml of tetrahydrofuran and 4 drops of water. The reaction mixture is stirred for 8 hours at room temperature. The reaction medium is concentrated and then diluted with 10 ml of water and washed with twice 10 ml of dichloromethane. The aqueous phase is acidified with 1N hydrochloric acid and then extracted with ethyl acetate. The organic phases are combined and dried over sodium sulfate. The solvents are evaporated off and the residue is then chromatographed on a preparative silica plate (95/5/0.5% dichloromethane/methanol/aqueous ammonia). 7.9 mg of 3-{5-[3-(1-methyl-3-pentylureido)phenyl]pyrimidin-2-yl}acrylic acid are obtained in the form of beige-colored crystals. Yield=22%.

$^1$H NMR (CDCl$_3$, 400 MHz): 0.88 (t, J=7 Hz, 3H); 1.27 (m, 4H); 1.42 (m, 2H); 3.18 (q, j=6.8 Hz, 2H); 3.37 (s, 3H); 4.41 (t, J=5.5 Hz, 1H); 6.67 (d, J=16.2 Hz, 1H); 7.44 (d, J=7.8 Hz, 1H); 7.58 (t, J=7.8 Hz, 1H); 7.76 (d, J=16.2 Hz, 1H); 8.42 (m, 2H); 8.99 (s, 2H).

EXAMPLE 10

Synthesis of 3-{5-[3-(1-methyl-3-pentylureido)phenyl]pyrimidin-2-yl}propanoic acid

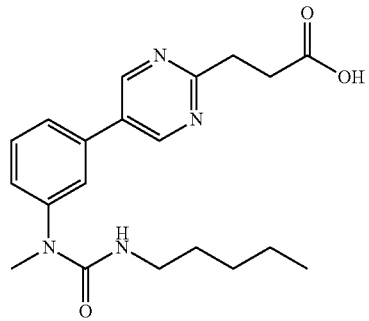 [SMILES: CCCCCNC(=O)N(C)c1cccc(-c2cnc(CCC(=O)O)nc2)c1]

a. Preparation of methyl 3-{5-[3-(tert-butoxycarbonylmethylamino)phenyl]pyrimidin-2-yl}propanoate 30 mg of 10% Pd/C are added to a solution of 0.3 g (0.81 mmol, 1 eq) of methyl 3-{5-[3-(tert-butoxycarbonylmethylamino)phenyl]pyrimidin-2-yl}acrylate (obtained as in 9c) in 3 ml of methanol, in a PARR bomb. The reaction mixture is placed under a hydrogen pressure of 3 bar and is then heated at 50° C. for 12 hours. The reaction medium is cooled to room temperature and then degassed with nitrogen and filtered through Celite. After evaporating off the solvents, the residue is chromatographed on silica gel (90/10 heptane/ethyl acetate). 118.2 mg of methyl 3-{5-[3-(tert-butoxycarbonylmethylamino)phenyl]pyrimidin-2-yl}propanoate are obtained in the form of a colorless oil. Yield=40%.

b. Preparation of methyl 3-[5-(3-methylaminophenyl)pyrimidin-2-yl]propanoate 0.12 ml (1.6 mmol, 5 eq) of trifluoroacetic acid is added to a solution of 118 mg (0.32 mmol, 1 eq) of methyl 3-{5-[3-(tert-butoxycarbonylmethylamino)phenyl]pyrimidin-2-yl}propanoate in 4 ml of dichloromethane. The reaction mixture is stirred for 16 hours at room temperature. The reaction is stopped by adding 20 mL of 1N sodium hydroxide solution and is then extracted with ethyl acetate. The organic phases are combined and dried over sodium sulfate. The solvents are evaporated off and the residue is then chromatographed on silica gel (99/1 dichloromethane/methanol). 163 mg of methyl 3-[5-(3-methylaminophenyl)pyrimidin-2-yl]propanoate are obtained in the form of a colorless oil. Yield=99%.

c. Preparation of methyl 3-{5-[3-(1-methyl-3-pentylureido)phenyl]pyrimidin-2-yl}propanoate 133 mg (0.66 mmol, 1.1 eq) of 4-nitrophenyl chloroformate are added to a solution, cooled to 0° C., of 163 mg (0.6 mmol, 1 eq) of 3-[5-(3-methylaminophenyl)pyrimidin-2-yl]propanoate and 0.1 ml (0.72 mmol, 1.2 eq) in 5 ml of dichloromethane. The reaction mixture is stirred for 12 hours at room temperature. The reaction is stopped by adding 20 ml of water, dried over sodium sulfate and filtered, and the solvents are evaporated off. The residue is taken up in 3 ml of dimethylformamide and 69 μl (0.6 mmol, 1 eq) of N-amylamine are then added. The reaction medium is heated at 80° C. for 4 hours and then poured onto ice and extracted with ethyl acetate. The organic phases are combined and dried over sodium sulfate, the solvents are concentrated and the residue is then chromatographed on silica gel (60/40 heptane/ethyl acetate).

111.9 mg of methyl 3-{5-[3-(1-methyl-3-pentylureido)phenyl]pyrimidin-2-yl}propanoate are obtained in the form of a yellow oil. Yield=48%.

d. Synthesis of 3-{5-[3-(1-methyl-3-pentylureido)phenyl]pyrimidin-2-yl}propanoic acid 1.44 ml (1.45 mmol, 5 eq) of lithium hydroxide are added to a solution of 111 mg (0.29 mmol, 1 eq) of methyl 3-{5-[3-(1-methyl-3-pentylureido)phenyl]pyrimidin-2-yl}propanoate in 3 mL of tetrahydrofuran. The reaction mixture is stirred for four hours at room temperature. The reaction is stopped by adding 10 ml of water, washed with ether and then acidified with 1N hydrochloric acid solution, and then extracted with ethyl acetate. The organic phases are combined and dried over sodium sulfate. The solvents are evaporated off and the residue is then crystallized from ether. 66.7 mg of 3-{5-[3-(1-methyl-3-pentylureido)phenyl]pyrimidin-2-yl}propanoic acid are obtained in the form of white crystals. Yield=48%.

$^1$H NMR (CDCl$_3$, 400 MHz): 0.84 (t, J=7.0 Hz, 3H); 1.25 (m, 4H); 1.39 (m, 2H); 2.78 (t, J=7.3 Hz, 2H); 3.03 (t, J=7.1, 2H); 3.17 (q, J=7.2 Hz, 2H); 3.19 (s, 3H); 4.41 (t, J=5.4 Hz, 1H); 7.38 (m, 1H); 7.55 (t, J=8 Hz, 1H); 8.35 (m, 2H); 8.75 (s, 2H).

EXAMPLE 11

Synthesis of 2-[2-butoxy-4-(2-carboxyethyl)phenyl]-6-(1-methyl-3-pentylureido)pyridinium hydrochloride

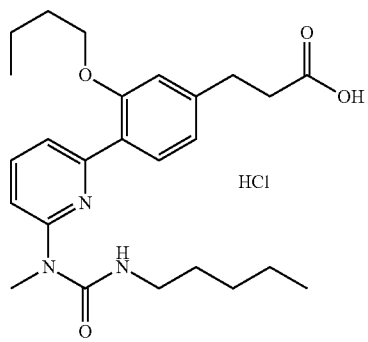 [SMILES: CCCCCNC(=O)N(C)c1cccc(-c2ccc(CCC(=O)O)cc2OCCCC)n1 ; Cl]

a. Preparation of 6-methylamino-2-bromopyridine 30 g (0.13 mol) of 2,6-dibromopyridine are added to a solution of 225 ml (2.39 mol) of methylamine in ethanol (33% by weight, Aldrich) precooled to 0° C. The reaction is heated at 80° C. with stirring for 20 hours, in a glass system equipped with a manometer. The reaction is monitored by TLC control. The reaction medium is cooled to 0° C. and the assembly is opened. The slightly brown solution thus obtained is concentrated under vacuum to a volume of 60 ml, and water (240 ml) is then added, followed by addition of aqueous sodium carbonate solution (2N, 240 ml). The beige-coloured precipitate formed is filtered off, washed with water and dissolved in dichloromethane (200 ml). The solution is dried over magnesium sulfate and the solvent is evaporated off. The addition of heptane allows the precipitation of 17.5 g (74%) of 6-methylamino-2-bromopyridine in the form of a beige-coloured powder.

b. Preparation of 1-(6-bromopyrid-2-yl)-1-methyl-3-pentylurea 2 g of 6-methylamino-2-bromopyridine are mixed with 3.0 mL of pentyl isocyanate. The mixture is heated for 12 hours at 100° C. The residue is chromatographed on silica (9/1 heptane/ethyl acetate). 1.8 g of 1-(6-bromopyrid-2-yl)-1-methyl-3-pentylurea are obtained. Yield=56%.

c. Preparation of methyl 3-butoxy-4-iodobenzoate 21.5 mL (0.189 mol, 1.5 eq) of 1-iodobutane are added to a solution of 35.03 g (0.126 mol, 1 eq) of methyl 3-hydroxy-3-iodobenzoate in 350 ml of methyl ethyl ketone in the presence of 52.24 g (0.378 mol, 3 eq) of potassium carbonate. The reaction medium is heated at 85° C. for 2 hours. The solid is filtered off and the solvent is evaporated off. The solid obtained is washed with heptane to give 41.78 g of methyl 3-butoxy-4-iodobenzoate in the form of white crystals. Yield=99%.

d. Preparation of 3-butoxy-4-iodophenyl)methanol 8.17 g (0.375 mol, 3 eq) of lithium borohydride are added to a solution of 41.78 g (0.125 mol, 1 eq) of methyl 3-butoxy-4-iodobenzoate in 210 ml of tetrahydrofuran. The reaction medium is heated at 60° C. for 2 hours and then hydrolyzed cautiously with ice-cold saturated ammonium chloride solution. The reaction medium is neutralized with concentrated hydrochloric acid and then extracted with ethyl acetate. The organic phases are washed with water and dried over magnesium sulfate. The solvent is evaporated off to give 38.31 g of (3-butoxy-4-iodophenyl)methanol in the form of a whitish oil. Yield=100%.

e. Preparation of 3-butoxy-4-iodobenzaldehyde 89.5 g (0.875 mol, 7 eq) of manganese dioxide are added to a solution of 38.30 g (0.125 mol, 1 eq) of (3-butoxy-4-iodophenyl)methanol in 250 mL of dichloromethane. The reaction medium is stirred at room temperature for 18 hours and then filtered through silica gel. The solvent is evaporated off to give 29.61 g of 3-butoxy-4-iodobenzaldehyde in the form of an orange-colored oil. Yield=78%.

f. Preparation of methyl (E)-3-(3-butoxy-4-iodophenyl)acrylate 65.08 g (0.195 mol, 2 eq) of methyl (triphenylphosphoranylidene)acetate are added to a solution of 29.60 g (0.097 mol, 1 eq) of 3-butoxy-4-iodobenzaldehyde in 360 ml of toluene. The reaction mixture is refluxed for 2 hours. The solvent is evaporated off and the oil obtained is chromatographed on silica gel (50/50 heptane/dichloromethane). 30.47 g of methyl (E)-3-(3-butoxy-4-iodophenyl)acrylate are obtained in the form of pale yellow crystals. Yield=87%.

g. Preparation of methyl(E)-3-[3-Butoxy-4-(4,4,5,5-tetramethyl[1,3,2]dioxaborolan-2-yl)phenyl]acrylate 2.0 g of methyl(E)-3-(3-butoxy-4-iodophenyl)acrylate are dissolved in 10 mL of dimethylformamide, and 1.8 g of pinacoldiborane are added, along with 226 mg of diphenylphosphinoferrocenepalladium dichloride and 1.6 g of potassium acetate. The mixture is stirred for 3 hours at 90° C. The reaction is hydrolyzed and extracted with ethyl acetate. After evaporation of the solvents and chromatography on silica gel (eluent=7/3 heptane/ethyl acetate), 1.10 g of methyl (E)-3-[3-butoxy-4-(4,4,5,5-tetramethyl[1,3,2]dioxaborolan-2-yl)phenyl]acrylate are obtained. Yield=55%.

h. Preparation of methyl (E)-3-{3-butoxy-4-[6-(1-methyl-3-pentylureido)pyrid-2-yl]phenyl}acrylate 496 mg of methyl(E)-3-[3-butoxy-4-(4,4,5,5-tetramethyl[1,3,2]dioxaborolan-2-yl)phenyl]acrylate are dissolved in 5 mL of dimethylformamide and 1 mL of 2N potassium phosphate solution. 350 mg of 1-(6-bromopyrid-2-yl)-1-methyl-3-phenylurea are added, along with 5 mg of palladium acetate and 16 mg of dicyclohexylbiphenylphosphine. The mixture is stirred for 3 hours at 90° C. and is then hydrolyzed and extracted with ethyl acetate. After evaporation of the solvents and chromatography on silica gel (eluent=7/3 heptane/ethyl acetate), 430 mg of methyl (E)-3-{3-butoxy-4-[6-(1-methyl-3-pentylureido)pyrid-2-yl]phenyl}acrylate are obtained. Yield=82%.

i. Preparation of methyl 3-{3-butoxy-4-[6-(1-methyl-3-pentylureido)pyrid-2-yl]phenyl}propionate A solution of 430 mg of methyl(E)-3-{3-butoxy-4-[6-(1-methyl-3-pentylureido)pyrid-2-yl]phenyl}acrylate in 5 mL of methanol is stirred for 3 hours at room temperature in the presence of 100 mg of palladium-on-charcoal, under a hydrogen atmosphere. After filtering off the palladium and evaporating off the solvents, 370 mg of methyl 3-{3-butoxy-4-[6-(1-methyl-3-pentylureido)pyrid-2-yl]phenyl}propionate are obtained. Yield=86%.

j. Synthesis of 2-[2-butoxy-4-(2-carboxyethyl)phenyl]-6-(1-methyl-3-pentylureido)pyridinium hydrochloride 300 mg of sodium hydroxide are added to a solution of 370 mg of methyl 3-{3-butoxy-4-[6-(1-methyl-3-pentylureido)pyrid-2-yl]phenyl}propionate dissolved in 15 ml of an 8/2 tetrahydrofuran/methanol mixture. After stirring for 4 hours at room temperature, the reaction is stopped with water and acetic acid and is then extracted with ethyl acetate. The solvents are evaporated off. The residual oil is chromatographed on silica gel (7/3 heptane/ethyl acetate). 5 mL of a solution of hydrogen chloride in ethyl acetate are added and the hydrochloride is precipitated by addition of isopropyl ether. After filtration, 205 mg of 2-[2-butoxy-4-(2-carboxyethyl)phenyl]-6-(1-methyl-3-pentylureido)pyridinium hydrochloride are obtained. Yield=53%.

$^1$H NMR (DMSO, 400 MHz): 0.80 (m, 3H); 0.93 (m, 3H); 1.24 (m, 4H); 1.44 (m, 4H); 1.74 (m, 2H); 2.64 (m, 2H); 2.92 (m, 2H); 3.39 (s, 3H); 4.10 (m, 2H); 6.98 (d, J=8 Hz, 1H); 7.13 (s, 1H); 7.24 (d, J=8 Hz, 1H); 7.56 (m, 2H); 7.97 (m, 1H); 9.70 (s, 1H).

EXAMPLE 12

Synthesis of 2-[2-butoxy-4-(2-carboxyethyl)phenyl]-6-(1-methyl-3-heptylureido)pyridinium hydrochloride

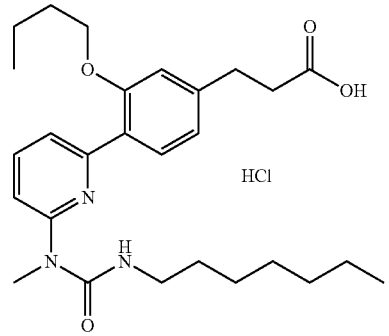 [SMILES: CCCCCCCNC(=O)N(C)c1cccc(-c2ccc(CCC(=O)O)cc2OCCCC)n1 ; Cl]

a. Preparation of (6-bromopyrid-2-yl)-1-methyl-3-heptylurea 2 g of 6-methylamino-2-bromopyridine (prepared according to the procedure of Example 11, step a) are mixed with 3.0 mL of heptyl isocyanate. The mixture is heated for 12 hours at 100° C. The residue is chromatographed on silica gel (9/1 heptane/ethyl acetate). 2.45 g of 1-(6-bromopyrid-2-yl)-1-methyl-3-heptylurea are obtained. Yield=71%.

b. Synthesis of 2-[2-butoxy-4-(2-carboxyethyl)phenyl]-6-(1-methyl-3-heptylureido)pyridinium hydrochloride 300 mg of sodium hydroxide are added to a solution of 377 mg of methyl 3-{3-butoxy-4-[6-(1-methyl-3-heptylureido)pyrid-2-yl]phenyl}propionate (prepared according to the procedure of Example 11, steps c to i, replacing the 1-(6-bromopyrid-2-yl)-1-methyl-3-pentylurea with 1-(6-bromopyrid-2-yl)-1-methyl-3-heptylurea in step h) dissolved in 15 mL of an 8/2 tetrahydrofuran/methanol mixture. After stirring for 4 hours at room temperature, the reaction is stopped with water and acetic acid and is then extracted with ethyl acetate. The solvents are evaporated off. The residual oil is chromatographed on silica gel (7/3 heptane/ethyl acetate). 5 mL of a solution of hydrogen chloride in ethyl acetate are added, and the hydrochloride is precipitated by addition of isopropyl ether. After filtration, 220 mg of 2-[2-butoxy-4-(2-carboxyethyl)phenyl]-6-(1-methyl-3-heptylureido)pyridinium hydrochloride are obtained. Yield=55%.

$^1$H NMR (DMSO, 400 MHz): 0.80 (m, 3H); 0.88 (m, 3H); 1.16 (m, 8H); 1.37 (m, 4H); 1.67 (m, 2H); 2.50 (m, 2H); 2.85 (m, 2H); 3.16 (m, 2H); 3.33 (s, 3H); 4.04 (m, 2H); 6.92 (d, J=8 Hz, 1H); 7.07 (s, 1H); 7.17 (d, J=8 Hz, 1H); 7.50 (m, 2H); 7.91 (m, 1H); 9.70 (s, 1H).

EXAMPLE 13

Synthesis of 2-[4-(2-carboxyethyl)-2-ethoxyphenyl]-6-(3-heptyl-1-methylureido)pyridinium hydrochloride

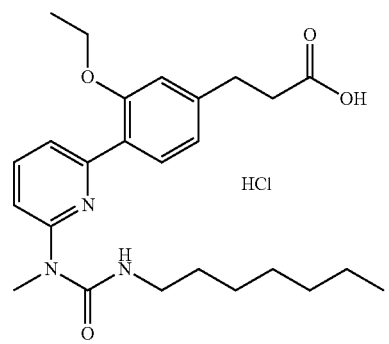 [SMILES: CCCCCCCNC(=O)N(C)c1cccc(-c2ccc(CCC(=O)O)cc2OCC)n1 ; Cl]

a. Preparation of 3-ethoxy-4-(4,4,5,5-tetramethyl[1,3,2]dioxaborolan-2-yl)benzaldehyde 2.0 g of ethylvanillin are dissolved in 10 mL of dichloromethane and 3 mL of triethylamine are then added. 2.36 mL of triflic anhydride are added slowly at 0° C. After stirring for 1 hour at 0° C., the reaction is hydrolyzed with sodium hydrogen carbonate solution and then extracted with ethyl acetate. After evaporating off the solvents, the oil obtained is dissolved in 20 ml of dimethylformamide, and 3.96 g of pinacoldiborane are added, along with 489 mg of diphenylphosphinoferrocenepalladium dichloride and 3.53 g of potassium acetate. The mixture is stirred for 3 hours at 90° C. The reaction is hydrolyzed and then extracted with ethyl acetate. The solvents are evaporated off and the residue obtained is chromatographed on silica gel (eluent=7/3 heptane/ethyl acetate). 1.62 g of 3-ethoxy-4-(4,4,5,5-tetramethyl[1,3,2]dioxaborolan-2-yl)benzaldehyde are obtained. Yield=49%.

b. Preparation of tert-butyl 6-(2-ethoxy-4-formylphenyl)pyrid-2-yl]methylcarbamate 1.62 g of 3-ethoxy-4-(4,4,5,5-tetramethyl[1,3,2]dioxaborolan-2-yl)benzaldehyde are dissolved in 15 mL of dimethylformamide, and 3 mL of 2M potassium phosphate solution and 2.52 g of tert-butyl (6-bromopyrid-2-yl)methylcarbamate are added, along with 64 mg of palladium acetate and 200 mg of dicyclohexylbiphenylphosphine. The mixture is stirred for 3 hours at 90° C. The reaction is hydrolyzed and then extracted with ethyl acetate. The solvents are evaporated off and the residue obtained is chromatographed on silica gel (eluent=7/3 heptane/ethyl acetate). 1.1 g of tert-butyl 6-(2-ethoxy-4-formylphenyl)pyrid-2-yl]methylcarbamate are obtained. Yield=53%.

c. Preparation of methyl (E)-3-{4-[6-(tert-butoxycarbonylmethylamino)pyrid-2-yl]-3-ethoxyphenyl}acrylate g of tert-butyl 6-(2-ethoxy-4-formylphenyl)pyrid-2-yl]methylcarbamate are dissolved in 10 ml of toluene and 1.55 g of methyl triphenylphosphoranylideneacetate are then added. The reaction mixture is stirred for 1 hour at 90° C. After evaporating off the solvent, the residual oil obtained is chromatographed on silica gel (8/2 heptane/ethyl acetate). 1.0 g of methyl (E)-3-{4-[6-(tert-butoxycarbonylmethylamino)pyrid-2-yl]-3-ethoxyphenyl}acrylate is obtained. Yield=78%.

d. Preparation of methyl 3-{4-(6-(tert-butoxycarbonylmethylamino)pyrid-2-A-3-ethoxyphenyl}propionate A solution of 1.0 g of methyl(E)-3-{4-[6-(tert-butoxycarbonylmethylamino)pyrid-2-yl]-3-ethoxyphenyl}acrylate in 10 mL of methanol is stirred for 3 hours at room temperature in the presence of 200 mg of 10% palladium-on-charcoal under a hydrogen atmosphere. After filtering off the palladium and evaporating off the solvents, 1.0 g of methyl 3-{4-[6-(tert-butoxycarbonylmethylamino)pyrid-2-yl]-3-ethoxyphenyl}propionate is obtained. Yield=100%.

e. Preparation of methyl 3-[3-ethoxy-4-(6-methylaminopyrid-2-yl)phenyl]propionate g of methyl 3-{4-[6-(tert-butoxycarbonylmethylamino)pyrid-2-yl]-3-ethoxyphenyl}propionate is dissolved in 10 mL of dichloromethane and 4 mL of trifluoroacetic acid are then added. The mixture is stirred for 48 hours at room temperature. After hydrolysis of the reaction with sodium hydrogen carbonate solution and then extraction with ethyl acetate, the solvents are evaporated off. 615 mg of methyl 3-[3-ethoxy-4-(6-methylaminopyrid-2-yl)phenyl]propionate are obtained. Yield=81%.

f. Preparation of methyl 3-{3-Ethoxy-4-[6-(3-heptyl-1-methylureido)pyrid-2-yl]phenyl}propionate 615 mg of methyl 3-[3-ethoxy-4-(6-methylaminopyrid-2-yl)phenyl]propionate are mixed with 1.0 mL of heptyl isocyanate. After microwave irradiation for one hour (T=100° C.), the mixture is chromatographed on silica gel (9/1 heptane/ethyl acetate). 735 mg of methyl 3-{3-ethoxy-4-[6-(3-heptyl-1-methylureido)pyrid-2-yl]phenyl}propionate are obtained. Yield=82%.

g. Synthesis of 2-[4-(2-carboxyethyl)-2-ethoxyphenyl]-6-(3-heptyl-1-methylureido)pyridinium hydrochloride 500 mg of sodium hydroxide are added to a solution of 735 mg of methyl 3-{3-ethoxy-4-[6-(3-heptyl-1-methylureido)pyrid-2-yl]phenyl}propionate dissolved in 15 ml of an 8/2 tetrahydrofuran/methanol mixture. After stirring for 4 hours at room temperature, the reaction is stopped with water and acetic acid and then extracted with ethyl acetate. The solvents are evaporated off. The residual oil is chromatographed on silica gel (7/3 heptane/ethyl acetate). 5 mL of a solution of hydrogen chloride in ethyl acetate are added to the chromatographed product and the hydrochloride is precipitated by addition of isopropyl ether. After filtration, 441 mg of 2-[4-(2-carboxyethyl)-2-ethoxyphenyl]-6-(3-heptyl-1-methylureido)pyridinium hydrochloride are obtained. Yield=57%.

$^1$H NMR (DMSO, 400 MHz): 0.85 (m, 3H); 1.18 (m, 8H); 1.37 (m, 3H); 1.48 (m, 2H); 2.64 (m, 2H); 2.92 (m, 2H); 3.25 (s, 3H); 4.20 (m, 2H); 6.98 (d, J=8 Hz, 1H); 7.12 (s, 1H); 7.25 (d, J=8 Hz, 1H); 7.58 (d, J=8 Hz, 2H); 7.99 (m, 1H); 9.70 (s, 1H).

EXAMPLE 14

Synthesis of 3-(3-butoxy-4-{5-[(methyloctanoylamino)methyl]thiophen-3-yl}phenyl)propanoic acid a. Preparation of (4-bromothiophen-2-ylmethyl)methylamine 10.6 g of 4-bromothiophene-2-carbaldehyde are dissolved in 100 mL of acetonitrile, and 11.8 g of methylamine hydrochloride and 6.28 g of sodium cyanoborohydride are added. The reaction mixture is stirred overnight at room temperature. The reaction is stopped with 1M sodium hydroxide solution. After evaporating off the solvents, the residue is chromatographed on silica gel (7/3 heptane/ethyl acetate). 8.19 g of (4-bromothiophen-2-ylmethyl)methylamine are obtained. Yield=79%.

b. Preparation of tert-butyl (4-bromothiophen-2-ylmethyl)methylcarbamate 8.18 g of (4-bromothiophen-2-ylmethyl)methylamine are dissolved in 80 ml of dichloromethane in the presence of 6.65 ml of triethylamine. At 0° C., a solution of 9.53 g of di-tert-butyl dicarbonate in 10 ml of dichloromethane is added slowly. The reaction mixture is stirred for 2 hours at room temperature. The reaction is stopped with water and is then extracted with ethyl acetate. After evaporating off the solvents, the residue is chromatographed on silica gel (7/3 heptane/ethyl acetate). 5.93 g of tert-butyl (4-bromothiophen-2-ylmethyl)methylcarbamate are obtained. Yield=49%.

c. Preparation of tert-butyl methyl-[4-(4,4,5,5-tetramethyl[1,3,2]dioxaborolan-2-yl)thiophen-2-ylmethyl]carbamate 5.92 g of tert-butyl (4-bromothiophen-2-ylmethyl)methylcarbamate are dissolved in 70 ml of dimethylformamide, and 5.89 g of pinacoldiborane are added along with 776 mg of diphenylphosphinoferrocenepalladium dichloride and 5.59 g of potassium acetate. The mixture is stirred for 3 hours at 90° C. The reaction is stopped with water and then extracted with ethyl acetate. The solvents are evaporated off. The residue is chromatographed on silica (eluent=7/3 heptane/ethyl acetate). 4.57 g of tert-butyl methyl-[4-(4,4,5,5-tetramethyl[1,3,2]dioxaborolan-2-yl)thiophen-2-ylmethyl]carbamate are obtained. Yield=63%.

d. Preparation of methyl (E)-3-(3-butoxy-4-(5-{[tert-butoxycarbonylmethylamino)methyl]thiophen-3-yl}phenyl)acrylate 2.50 g of tert-butyl methyl-[4-(4,4,5,5-tetramethyl[1,3,2]dioxaborolan-2-yl)thiophen-2-ylmethyl]carbamate are dissolved in 27 ml of dimethylformamide, and 5.5 mL of 2M potassium phosphate solution and 1.96 g of methyl (E)-3-(3-butoxy-4-iodophenyl)acrylate (prepared according to the procedure of Example 11, step f), are added, along with 12 mg of palladium acetate and 38 mg of dicyclohexylbiphenylphosphine. The mixture is stirred for 1 hour at 90° C. The reaction is stopped with water and then extracted with ethyl acetate. The solvents are evaporated off. The residue is chromatographed on silica (eluent=7/3 heptane/ethyl acetate). 1.98 g of methyl (E)-3-(3-butoxy-4-{5-[(tert-butoxycarbonylmethylamino)methyl]thiophen-3-yl}phenyl)acrylate are obtained. Yield=79%.

e. Preparation of methyl (E)-3-(3-butoxy-4-{5-[(tert-butoxycarbonylmethylamino)methyl]thiophen-3-yl}phenyl)propionate 1.98 g of methyl (E)-3-(3-butoxy-4-{5-[(tert-butoxycarbonylmethylamino)methyl]thiophen-3-yl}phenyl)acrylate are dissolved in 20 ml of methanol and stirred for 12 hours at room temperature in the presence of 1.0 g of palladium-on-charcoal under a hydrogen atmosphere. After filtering off the palladium and evaporating off the solvents, 1.37 g of methyl (E)-3-(3-butoxy-4-{5-[(tert-butoxycarbonylmethylamino)methyl]thiophen-3-yl}phenyl)propionate are obtained. Yield=69%.

f. Preparation of methyl 3-[3-butoxy-4-(5-methylaminomethylthiophen-3-yl)phenyl]propionate 1.36 g of methyl (E)-3-(3-butoxy-4-{5-[(tert-butoxycarbonylmethylamino)methyl]thiophen-3-yl}phenyl)propionate are dissolved in 15 ml of dichloromethane and 2.2 ml of trifluoroacetic acid are then added. The mixture is stirred for 2 hours at room temperature. After hydrolyzing the reaction with sodium hydrogen carbonate solution and then extracting with ethyl acetate and evaporating off the solvents, 1.15 g of methyl 3-[3-butoxy-4-(5-methylaminomethylthiophen-3-yl)phenyl]propionate are obtained. Yield=100%.

g. Preparation of methyl 3-(3-butoxy-4-{5-[(methyloctanoylamino)methyl]thiophen-3-yl}phenyl)propionate 1.07 g of methyl 3-[3-butoxy-4-(5-methylaminomethylthiophen-3-yl)phenyl]propionate are dissolved in 20 mL of dichloromethane, and 1.25 mL of triethylamine are added, along with 36 mg of dimethylaminopyridine. 318 mg of octanoyl chloride are added. The reaction mixture is stirred for 12 hours at room temperature. After hydrolyzing the reaction with sodium hydrogen carbonate solution and then extracting with ethyl acetate and evaporating off the solvents, a crude product is obtained, which is chromatographed on silica gel (eluent=7/3 heptane/ethyl acetate). 432 mg of methyl 3-(3-butoxy-4-{5-[(methyloctanoylamino)methyl]thiophen-3-yl}phenyl)propionate are obtained. Yield=81%.

h. Synthesis of 3-(3-butoxy-4-{5-[(methyloctanoylamino)methyl]thiophen-3-yl}phenyl)propanoic acid 350 mg of sodium hydroxide are added to a solution of 427 mg of methyl 3-(3-butoxy-4-{5-[(methyloctanoylamino)methyl]thiophen-3-yl}phenyl)propionate dissolved in 10 mL of methanol. After stirring for 2 hours at 40° C., the reaction is hydrolyzed with hydrochloric acid solution and then extracted with ethyl acetate. The solvents are evaporated off. The residual oil is crystallized from a heptane/ethyl ether mixture.

318 mg of 3-(3-butoxy-4-{5-[(methyloctanoylamino)methyl]thiophen-3-yl}phenyl)propanoic acid are obtained. Yield=77%.

$^1$H NMR (CDCl$_3$, 400 MHz): 0.85 (m, 3H); 1.28 (m, 8H); 1.49 (m, 2H); 1.60 (m, 2H); 1.79 (m, 2H); 2.33&2.48 (2m (rotamers), 2H); 2.65 (m, 2H); 2.95 (m, 2H); 2.99 (s, 3H); 4.00 (m, 2H); 4.65&4.72 (2s(rotamers), 2H); 6.80 (m, 2H); 7.27 (m, 2H); 7.37 (m, 1H); 7.49 (m, 1H).

EXAMPLE 15

Synthesis of 3-[3-butoxy-4-(5-{[(4-methoxybenzoyl)methylamino]methyl}thiophen-3-yl)phenyl]propanoic acid

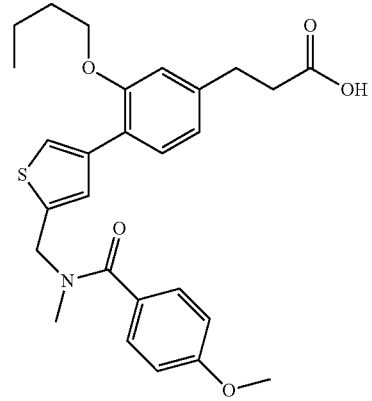 [SMILES: CCCCOc1cc(CCC(=O)O)ccc1-c1csc(CN(C)C(=O)c2ccc(OC)cc2)c1]

a. Preparation of methyl 3-[3-butoxy-4-(5-{[(4-methoxybenzoyl)methylamino]methyl}thiophen-3-yl)phenyl]propionate 1.07 g of methyl 3-[3-butoxy-4-(5-methylaminomethylthiophen-3-yl)phenyl]propionate (prepared according to the procedure of Example 14, steps a to f) are dissolved in 20 ml of dichloromethane, and 1.25 ml of triethylamine are added, along with 36 mg of dimethylaminopyridine. 270 mg of 4-methoxybenzoyl chloride are added. The reaction mixture is stirred for 12 hours at room temperature. The reaction is stopped with sodium hydrogen carbonate solution and then extracted with ethyl acetate. The solvents are evaporated off. The residue is chromatographed on silica (eluent=7/3 heptane/ethyl acetate).

388 mg of methyl 3-[3-butoxy-4-(5-{[(4-methoxybenzoyl)methylamino]methyl}thiophen-3-yl)phenyl]propionate are obtained. Yield=71%.

b. Synthesis of 3-[3-butoxy-4-(5-{[(4-methoxybenzoyl)methylamino]methyl}thiophen-3-yl)phenyl]propanoic acid 308 mg of sodium hydroxide are added to a solution of 382 mg of methyl 3-[3-butoxy-4-(5-{[(4-methoxybenzoyl)methylamino]methyl}thiophen-3-yl)phenyl]propionate dissolved in 10 mL of methanol. After stirring for 2 hours at 40° C., the reaction is hydrolyzed with hydrochloric acid solution and then extracted with ethyl acetate. The solvents are evaporated off. The residual oil is crystallized from a heptane/ethyl ether mixture.

300 mg of 3-[3-butoxy-4-(5-{[(4-methoxybenzoyl)methylamino]methyl}thiophen-3-yl)phenyl]propanoic acid are obtained. Yield=81%.

$^1$H NMR (CDCl$_3$, 400 MHz): 0.95 (m, 3H); 1.47 (m, 2H); 1.79 (m, 2H); 2.70 (m, 2H); 2.96 (m, 2H); 3.09 (s, 3H); 3.82 (s, 3H); 4.00 (m, 2H); 4.79 (s, 2H); 6.81 (m, 2H); 6.88 (m, 3H); 7.24-7.52 (m, 4H).

EXAMPLE 16

Synthesis of 3-[3-butoxy-4-(5-{[(3-methoxybenzoyl)methylamino]methyl}thiophen-3-yl)phenyl]propanoic acid

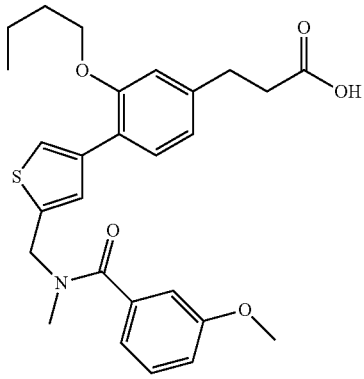 [SMILES: CCCCOc1cc(CCC(=O)O)ccc1-c1csc(CN(C)C(=O)c2cccc(OC)c2)c1]

a. Preparation of methyl 3-[3-butoxy-4-(5-{[(3-methoxybenzoyl)methylamino]methyl}thiophen-3-yl)phenyl]propionate 1.07 g of methyl 3-[3-butoxy-4-(5-methylaminomethylthiophen-3-yl)phenyl]propionate (prepared according to the procedure of Example 14, steps a to f) are dissolved in 20 mL of dichloromethane, and 1.25 ml of triethylamine are added, along with 36 mg of dimethylaminopyridine. 270 mg of 3-methoxybenzoyl chloride are added. The reaction mixture is stirred for 12 hours at room temperature. The reaction is stopped with sodium hydrogen carbonate solution and then extracted with ethyl acetate. The solvents are evaporated off. The residue is chromatographed on silica (eluent=7/3 heptane/ethyl acetate).

380 mg of methyl 3-[3-butoxy-4-(5-{[(3-methoxybenzoyl)methylamino]methyl}thiophen-3-yl)phenyl]propionate are obtained. Yield=70%.

b. Synthesis of 3-[3-butoxy-4-(5-{[(3-methoxybenzoyl)methylamino]methyl}thiophen-3-yl)phenyl]propanoic acid 302 mg of sodium hydroxide are added to a solution of 374 mg of methyl 3-[3-butoxy-4-(5-{[(3-methoxybenzoyl)methylamino]methyl}thiophen-3-yl)phenyl]propionate dissolved in 10 mL of methanol. After stirring for 2 hours at 40° C., the reaction is hydrolyzed with hydrochloric acid solution and then extracted with ethyl acetate. The solvents are evaporated off. The residual oil is crystallized from a heptane/ethyl ether mixture.

307 mg of 3-[3-butoxy-4-(5-{[(3-methoxybenzoyl)methylamino]methyl}thiophen-3-yl)phenyl]propanoic acid are obtained. Yield=84%.

$^1$H NMR (CDCl$_3$, 400 MHz): 0.95 (m, 3H); 1.47 (m, 2H); 1.79 (m, 2H); 2.69 (m, 2H); 2.96 (m, 2H); 3.10 (s, 3H); 3.81 (s, 3H); 4.00 (m, 2H); 4.62 & 4.88 (2s(rotamers), 2H); 6.81 (m, 2H); 6.96 (m, 3H); 7.26-7.52 (m, 4H).

EXAMPLE 17

Crossover-Curve PPAR Transactivation Tests

The activation of PPAR receptors with an agonist (activator) in HeLN cells leads to the expression of a reporter gene, luciferase, which, in the presence of a substrate, generates light. The modulation of the PPAR receptors is measured by quantifying the luminescence produced after incubating the cells in the presence of a reference agonist. The ligands displace the agonist from its site. The measurement of the activity is performed by quantifying the light produced. This measurement makes it possible to determine the modulatory activity of the compounds according to the invention by determining the constant that is the affinity of the molecule for the PPAR receptor. Since this value can fluctuate depending on the basal activity and the expression of the receptor, it is referred to as Kd apparent (KdApp in nM).

To determine this constant, "crossover curves" of the test product against a reference agonist are performed in a 96-well plate: 10 concentrations of the test product plus a concentration 0 are arranged in a line, and 7 concentrations of the agonist plus a concentration 0 are arranged in a column. This is 88 measurement points for 1 product and 1 receptor. The remaining 8 wells are used for repeatability controls.

In each well, the cells are in contact with a concentration of the test product and a concentration of the reference agonist, 2-(4-{2-[3-(2,4-difluorophenyl)-1-heptylureido]ethyl}phenylsulfanyl)-2-methylpropionic acid for PPARα, {2-methyl-4-[4-methyl-2-(4-trifluoromethylphenyl)thiazol-5-ylmethylsulfanyl]phenoxy}acetic acid for PPARδ and 5-{4-[2-(methylpyrid-2-ylamino)ethoxy]benzyl}thiazolidine-2,4-dione for PPARγ. Measurements are also taken for total agonist controls with the same products.

The HeLN cell lines used are stable transfectants containing the plasmids ERE-βGlob-Luc-SV-Neo (reporter gene) and PPAR (α, δ, γ) Gal-hPPAR. These cells are inoculated into 96-well plates at a rate of 10 000 cells per well in 100 μl of DMEM medium without phenol red and supplemented with 10% of defatted calf serum. The plates are then incubated at 37° C. and 7% CO$_2$ for 16 hours.

The various dilutions of the test products and of the reference ligand are added at a rate of 5 μl per well. The plates are then incubated for 18 hours at 37° C. and 7% CO$_2$. The culture medium is removed by turning over and 100 μl of a 1:1 PBS/luciferine mixture are added to each well. After 5 minutes, the plates are read by the luminescence detector.

These crossed curves make it possible to determine the AC50 values (concentration at which 50% activation is observed) of the reference ligand at various concentrations of test product. These AC50 values are used to calculate the Schild regression by plotting a straight line corresponding to the Schild equation ("Quantitation in Receptor Pharmacology" Terry P. Kenakin, *Receptors and Channels*, 2001, 7, 371-385) which allows the Kd app values (in nM) to be obtained.

Transactivation Results:

| Compounds | PPARα Kd app (nM) | PPARδ Kd app (in nM) | PPARγ Kd app (in nM) |
|---|---|---|---|
| Reference 1: 2-(4-{2-[3-(2,4-difluorophenyl)-1-heptylureido]ethyl}phenylsulfanyl)-2-methylpropanoic acid | 200 | n.a. | n.a. |
| Reference 2: {2-methyl-4-[4-methyl-2-(4-trifluoromethylphenyl)thiazol-5-ylmethylsulfanyl]phenoxy}acetic acid | n.a. | 10 | n.a. |
| Reference 3: 5-{4-[2-(methylpyrid-2-ylamino)ethoxy]benzyl}thiazolidine-2,4-dione | n.a. | n.a. | 30 |
| Compound of Example 1 | n.a. | n.a. | 1000 |
| Compound of Example 6 | n.a. | 4000 | 250 |
| Compound of Example 2 | n.a. | n.a. | 500 |
| Compound of Example 7 | n.a. | n.a. | 60 |
| Compound of Example 8 | n.a. | n.a. | 1000 |
| Compound of Example 11 | 2000 | n.a. | 120 |
| Compound of Example 12 | 4000 | n.a. | 15 |
| Compound of Example 13 | 4000 | 8000 | 120 |
| Compound of Example 14 | n.a. | n.a. | 2 |
| Compound of Example 15 | n.a. | n.a. | 30 |
| Compound of Example 16 | n.a. | n.a. | 30 | n.a. means not active

These results show the affinity of the compounds for PPARγ and more particularly the specificity of the affinity of the compounds of the invention for the PPARγ subtype, compared with the affinity of the compounds for the PPARα subtype or for the PPARγ subtype.

EXAMPLE 18

Compositions

Various specific formulations based on the compounds according to the invention are illustrated in this example.

A—Oral Route:
(a) 0.2 g Tablet:

| | |
|---|---|
| Compound of Example 1 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable Suspension in 5 ml Ampules:

| | |
|---|---|
| Compound of Example 5 | 0.001 g |
| Glycerol | 0.500 g |
| 70% Sorbitol | 0.500 g |
| Sodium saccharinate | 0.010 g |
| Methyl para-hydroxybenzoate | 0.040 g |
| Flavoring | qs |
| Purified water | qs 5 ml |

(c) 0.8 g Tablet:

| | |
|---|---|
| Compound of Example 2 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable Suspension in 10 ml Ampules:

| | |
|---|---|
| Compound of Example 4 | 0.200 g |
| Glycerol | 1.000 g |
| 70% Sorbitol | 1.000 g |
| Sodium saccharinate | 0.010 g |
| Methyl para-hydroxybenzoate | 0.080 g |
| Flavoring | qs |
| Purified water | qs 10 ml |

B—Topical Route:
(a) Ointment:

| | |
|---|---|
| Compound of Example 6 | 0.020 g |
| Isopropyl myristate | 81.700 g |
| Liquid petroleum jelly fluid | 9.100 g |
| Silica ("Aerosil 200" marketed by Degussa) | 9.180 g |

(b) Ointment:

| | |
|---|---|
| Compound of Example 2 | 0.150 g |
| Compound of Example 4 | 0.150 g |
| White petroleum jelly codex | qs 100 g |

(c) Nonionic Water-in-Oil Cream:

| | |
|---|---|
| Compound of Example 1 | 0.100 g |
| Mixture of emulsifying lanolin alcohols, waxes and oils ("Anhydrous Eucerin" marketed by BDF) | 39.900 g |
| Methyl para-hydroxybenzoate | 0.075 g |
| Propyl para-hydroxybenzoate | 0.075 g |
| Sterile demineralized water | qs 100 g |

(d) Lotion:

| | |
|---|---|
| Compound of Example 3 | 0.100 g |
| Polyethylene glycol (PEG 400) | 69.900 g |
| 95% Ethanol | 30.000 g |

(e) Hydrophobic Ointment:

| | |
|---|---|
| Compound of Example 5 | 0.300 g |
| Isopropyl myristate | 36.400 g |
| Silicone oil ("Rhodorsil 47 V 300" marketed by Rhone-Poulenc) | 36.400 g |
| Beeswax | 13.600 g |
| Silicone oil ("Abil 300,000 cst" marketed by Goldschmidt) | qs 100 g |

(f) Nonionic Oil-in-Water Cream:

| | |
|---|---|
| Compound of Example 2 | 1.000 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A biaromatic compound having the following general formula (I):

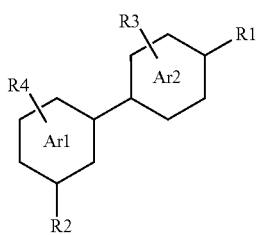

in which:
one of Ar1 and Ar2 is phenyl and the other is thiophene,
R1 is a radical of formula (a) or (b) below:

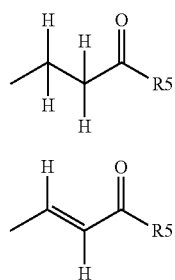

wherein R5 is as defined below;
R2 is a radical of formula $(CH_2)_m$—$NR_6$—CQ—$(NH)_n R_7$, wherein Q, R6, R7, m and n are as defined below;
R3 and R4, which may be identical or different, are each a hydrogen atom, a halogen atom, a linear or cyclic alkyl radical having from 1 to 12 carbon atoms that may be interrupted with oxygen, fluorine or nitrogen atoms, a hydroxyl radical, an alkoxy radical having from 1 to 10 carbon atoms, a polyether radical, an aralkyl radical or an aryloxy radical;
R5 is a hydroxyl radical, a radical OR8 or a hydroxylamine radical, wherein R8 is as defined below;
R6 is a lower alkyl radical having from 1 to 4 carbon atoms;
R7 is an alkyl radical having from 1 to 12 carbon atoms, an aryl radical, an aralkyl radical, a heteroaryl radical or a heterocyclic radical;
R8 is an alkyl, aryl or aralkyl radical;
m and n have the values 0 or 1;
Q is an oxygen or sulfur atom;
R9 is a hydrogen atom or an alkyl radical having from 1 to 12 carbon atoms; or an optical or geometrical isomer of said compound of formula (I), or a salt thereof.

2. The biaromatic compound as defined by claim 1, wherein formula (I), R1 is a radical of formula (a).

3. The biaromatic compound as defined by claim 1, wherein formula (I), R1 is a radical of formula (b).

4. The biaromatic compound as defined by claim 1, wherein formula (I), R5 is a hydroxyl radical.

5. The biaromatic compound as defined by claim 1, wherein formula (I), R5 is a radical OR8.

6. The biaromatic compound as defined by claim 1, wherein formula (I), R5 is a hydroxylamine radical.

7. The biaromatic compound as defined by claim 1, wherein formula (I), Q is an oxygen atom.

8. The biaromatic compound as defined by claim 1, wherein formula (I), Q is a sulfur atom.

9. The biaromatic compound as defined by claim 1, being a salt of an alkali metal or alkaline-earth metal or a salt of an organic amine.

10. The biaromatic compound as defined by claim 1, having at least one halogen atom substituent.

11. The biaromatic compound as defined by claim 1, having at least one methyl, ethyl, isopropyl, butyl, isobutyl, tert-butyl, hexyl, heptyl, octyl, decyl, cyclopentyl, cyclohexyl or methylenecyclopropyl radical substituent.

12. The biaromatic compound as defined by claim 1, having at least one methyl, ethyl, n-propyl, i-propyl, cyclopropyl, methylcyclopropyl, n-butyl, i-butyl or t-butyl radical substituent.

13. The biaromatic compound as defined by claim 1, having at least one methoxy, ethoxy, isopropyloxy, methylcyclopropyloxy, isobutoxy, tert-butoxy, pentyloxy, isopentyloxy, hexyloxy, heptyloxy, benzyloxy, aryloxy or phenoxy radical substituent, which may optionally be substituted with an alkyl radical having from 1 to 12 carbon atoms or an alkoxy radical having from 1 to 5 carbon atoms.

14. The biaromatic compound as defined by claim 1, having at least one methoxymethoxy, ethoxymethoxy or methoxyethoxymethoxy radical substituent.

15. The biaromatic compound as defined by claim 1, having at least one benzyl, phenethyl or 2-naphthylmethyl radical substituent, which may be mono- or disubstituted with a halogen atom, a $CF_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

16. The biaromatic compound as defined by claim 1, having at least one phenyl, biphenl, cinnamyl or naphthyl radical substituent, which may be mono- or disubstituted with a halogen atom, a $CF_3$ radical, an alkyl radical having from 1 to 12 carbon atoms, an alkoxy radical having from 1 to 7 carbon atoms, a nitro function, a polyether radical, an aryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

17. The biaromatic compound as defined by claim 1, having at least one furyl, thienyl, isoxazolyl, oxadiazolyl, oxazolyl, isothiazolyl, quinazolinyl, benzothiadiazolyl, benzimidazolyl, quinoxalyl, indolyl or benzofuryl radical substituent, optionally substituted with at least one halogen atom, an alkyl radical having from 1 to 12 carbon atoms, an alkoxy having from 1 to 7 carbon atoms, an aryl radical, a nitro function, a polyether radical, a heteroaryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

18. The biaromatic compound as defined by claim 1, having at least one morpholino, piperidino, piperazino, 2-oxo-1-piperidyl or 2-oxo-1-pyrrolidinyl radical substituent, optionally substituted with at least one alkyl radical having from 1 to 12 carbon atoms, an alkoxy radical having from 1 to 7 carbon atoms, an aryl radical, a nitro function, a polyether radical, a heteroaryl radical, a benzoyl radical, an alkyl ester group, a carboxylic acid, a hydroxyl radical optionally protected with an acetyl or benzoyl group or an amino function optionally protected with an acetyl or benzoyl group or optionally substituted with at least one alkyl radical having from 1 to 12 carbon atoms.

19. The biaromatic compound as defined by claim 1, selected from the group consisting of:
3-(5-{3-[(Methyloctanoylamino)methyl]phenyl}thiophen-2-yl)acrylic acid,
3-(5-{3-[(Methyloctanoylamino)methyl]phenyl}thiophen-2-yl)propanoic acid,
3-(4-{5-[(Methyloctanoylamino)methyl]thiophen-3-yl}phenyl)acrylic acid,
3-(4-{5-[(Methyloctanoylamino)methyl]thiophen-3-yl}phenyl)propanoic acid,
3-(3-Butoxy-4-{5-[(methyloctanoylamino)methyl]thiophen-3-yl}phenyl)propanoic acid,
3-[3-Butoxy-4-(5-{[(4-methoxybenzoyl)methylamino]methyl}thiophen-3-yl)phenyl]propanoic acid,
3-[3-Butoxy-4-(5-{[(3-methoxybenzoyl)methylamino]methyl}thiophen-3-yl)phenyl]propanoic acid, 3-(2-Fluoro-4-{5-[(heptanoylmethylamino)methyl]thiophen-3-yl}phenyl)propanoic acid,
3-(4-{5-[(Heptanoylmethylamino)methyl]thiophen-3-yl}-3-isobutoxyphenyl)acrylic acid,
3-(3-(2-Cyclopentylethoxy)-4-{5-[(methyloctanoylamino)methyl]thiophen-3-yl}phenyl)propanoic acid,
Methyl 3-(3-isobutoxy-4-{5-[(methylnonanoylamino)methyl]thiophen-3-yl}phenyl)propanoate,
3-(2-Chloro-4-{4-[(methylnonanoylamino)methyl]thiophen-2-yl}phenyl)propanoic acid,
3-(2-Fluoro-4-{4-[(methylnonanoylamino)methyl]thiophen-2-yl}phenyl)acrylic acid,
3-(5-{3-[(Methyloctanoylamino)methyl]phenyl}-4-propylthiophen-2-yl)propanoic acid,
3-(3-Benzyloxy-4-{5-[(methyloctanoylamino)methyl]thiophen-3-yl}phenyl)propanoic acid,
3-(4-Benzyl-5-{3-[(hexanoylmethylamino)methyl]phenyl}thiophen-2-yl)propanoic acid,
3-{4-Cyclopropylmethyl-5-[3-(1-methyl-3-pentylureido)phenyl]thiophen-2-yl}propanoic acid,
3-{5-[3-(1-Methyl-3-pentylureido)-4-trifluoromethylphenyl]thiophen-2-yl}propanoic acid,
3-(5-{3-[3-(4-Butoxyphenyl)-1-ethylureido]phenyl}thiophen-2-yl)propanoic acid,
and mixtures thereof.

20. The biaromatic compound as defined by claim 1, wherein formula (I) at least one of the following conditions is satisfied:
R3 is an alkoxy radical having from 1 to 7 carbon atoms;
R5 is a hydroxyl radical;
in the sequence $—(CH_2)_m—NR_6—CQ(NH)_nR_7$, m=0, n=1;
Q is an oxygen atom;
R7 is an alkyl radical having from 1 to 8 carbon atoms.

21. The biaromatic compound as defined by claim 1, wherein formula (I) all of the following conditions are satisfied:
R3 is an alkoxy radical having from 1 to 7 carbon atoms;
R5 is a hydroxyl radical;
in the sequence $—(CH_2)_m—NR_6—CQ(NH)_nR_7$, m=0, n=1;
Q is an oxygen atom;
R7 is an alkyl radical having from 1 to 8 carbon atoms.

22. A cosmetic composition comprising a cosmetically effective amount of at least one biaromatic compound as defined by claim 1, formulated into a cosmetically and physiologically acceptable support therefor.

23. The cosmetic composition as defined by claim 22, comprising from 0.0001% to 2% by weight of said at least one biaromatic compound.

24. The cosmetic composition as defined by claim 22, formulated for body or hair hygiene.

25. A pharmaceutical composition comprising a pharmaceutically effective amount of at least one biaromatic compound as defined by claim 1, formulated into a pharmaceutically and physiologically acceptable support therefor.

26. The pharmaceutical composition as defined by claim 25, comprising from 0.001% to 10% by weight of said at least one biaromatic compound.

27. A method for activating PPARγ receptors, said method comprising contacting said receptors with an effective PPARγ receptor activating amount of the biaromatic compound as defined by claim 1.

* * * * *